(12) United States Patent
Qin et al.

(10) Patent No.: US 12,116,350 B2
(45) Date of Patent: *Oct. 15, 2024

(54) COMPOUNDS FOR TREATING ILK-MEDIATED DISEASES

(71) Applicant: The Cleveland Clinic Foundation, Cleveland, OH (US)

(72) Inventors: Jun Qin, Solon, OH (US); Koichi Fukuda, Cleveland Heights, OH (US); Julia Vaynberg, Rocky River, OH (US); Suguna Rachakonda, Copley, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 53 days.

This patent is subject to a terminal disclaimer.

(21) Appl. No.: 18/051,762

(22) Filed: Nov. 1, 2022

(65) Prior Publication Data

US 2023/0127636 A1    Apr. 27, 2023

Related U.S. Application Data

(63) Continuation of application No. 16/963,968, filed as application No. PCT/US2019/014500 on Jan. 22, 2019, now Pat. No. 11,524,945.

(60) Provisional application No. 62/621,941, filed on Jan. 25, 2018.

(51) Int. Cl.
| | |
|---|---|
| C07D 239/70 | (2006.01) |
| A61K 31/517 | (2006.01) |
| A61K 31/519 | (2006.01) |
| A61K 31/52 | (2006.01) |
| A61K 45/06 | (2006.01) |
| A61P 35/00 | (2006.01) |
| C07D 239/94 | (2006.01) |

(52) U.S. Cl.
CPC ............ *C07D 239/94* (2013.01); *A61K 45/06* (2013.01); *A61P 35/00* (2018.01)

(58) Field of Classification Search
CPC .. C07D 239/70; C07D 239/94; A61K 31/517; A61K 31/519; A61K 31/52; A61P 35/00
See application file for complete search history.

(56) References Cited

U.S. PATENT DOCUMENTS

| | | | |
|---|---|---|---|
| 5,747,498 | A | 5/1998 | Schnur et al. |
| 8,309,133 | B2 | 11/2012 | Liversidge et al. |
| 8,575,339 | B2 | 11/2013 | Cheng |
| 9,133,137 | B2 | 9/2015 | Tung |
| 2010/0143295 | A1 | 6/2010 | Gant et al. |
| 2017/0247339 | A1 | 8/2017 | Hong et al. |

FOREIGN PATENT DOCUMENTS

| | | |
|---|---|---|
| EP | 2628011 | 8/2013 |
| WO | WO 2014/028914 | 2/2014 |

OTHER PUBLICATIONS

International Search Report and Written Opinion for PCT/US19/14500. Mailed Apr. 10, 2019. 15 pages.
Extended European Search Report for PCT/U.S. Pat. No. 2019014500. Mailed Aug. 20, 2021. 7 pages.
Agouni et al., Parathyroid hormone-related protein induces cell survival in human renal cell carcinoma through the PI3K Akt pathway: evidence for a critical role for integrin-linked kinase and nuclear factor kappa B. Carcinogenesis. Sep. 2007;28(9):1893-901.
Augustin et al., Quantitative chemical proteomics profiling differentiates erlotinib from gefitinib in EGFR wild-type non-small cell lung carcinoma cell lines. Mol Cancer Ther. Apr. 2013;12(4):520-9.
Bravou et al., ILK over-expression in human colon cancer progression correlates with activation of beta-catenin, down-regulation of E-cadherin and activation of the Akt-FKHR pathway. J Pathol. Jan. 2006;208(1):91-9.
Cabodi et al., Integrin signalling adaptors: not only figurants in the cancer story. Nat Rev Cancer. Dec. 2010;10(12):858-70.
Conradt et al., Disclosure of erlotinib as a multikinase inhibitor in pancreatic ductal adenocarcinoma. Neoplasia. Nov. 2011;13(11):1026-34.
Dai et al., Increased expression of integrin-linked kinase is correlated with melanoma progression and poor patient survival. Clin Cancer Res. Oct. 1, 2003;9(12):4409-14.
Das et al., Discovery of new quinazoline derivatives as irreversible dual EGFR/HER2 inhibitors and their anticancer activities—Part 1. Bioorganic & Medicinal Chemistry Letters 2019, 29(4): 591-596.
De La Puente et al., Identification of ILK as a novel therapeutic target for acute and chronic myeloid leukemia. Leuk Res. Sep. 9, 2015;S0145-2126(15)30377-5.
Denkert et al., Molecular alterations in triple-negative breast cancer-the road to new treatment strategies. Lancet. Jun. 17, 2017;389(10087):2430-2442.
Durbin et al., Oncogenic ILK, tumor suppression and all that JNK. Cell Cycle. Dec. 15, 2009;8(24):4060-6.
Fukuda et al., Biochemical, proteomic, structural, and thermodynamic characterizations of integrin-linked kinase (ILK): cross-validation of the pseudokinase. J Biol Chem. Jun. 17, 2011;286(24):21886-95.
Fukuda et al., The pseudoactive site of ILK is essential for its binding to alpha-Parvin and localization to focal adhesions. Mol Cell. Dec. 11, 2009;36(5):819-30.

(Continued)

*Primary Examiner* — Bruck Kifle
(74) *Attorney, Agent, or Firm* — Casimir Jones, S.C.; Anne M. Reynolds

(57) ABSTRACT

The present invention relates to compounds that are modulators of Integrin Linked Kinase (ILK), and methods of treating diseases with such compounds. In certain embodiments, the compounds are within Formulas I-VII (e.g., Csbl-1). In some embodiments, the compounds are used to treat an ILK-mediated disease, such as cancer (e.g., triple negative breast cancer) or an inflammatory disease.

11 Claims, 8 Drawing Sheets

(8 of 8 Drawing Sheet(s) Filed in Color)

(56) References Cited

OTHER PUBLICATIONS

Gazit et al., Tyrphostins IV—highly potent inhibitors of EGF receptor kinase. Structure-activity relationship study of 4-anilidoquinazolines. Bioorg Med Chem. Aug. 1996;4(8):1203-7.

Han et al., Targeting Integrin-Linked Kinase Suppresses Invasion and Metastasis through Downregulation of Epithelial-to-Mesenchymal Transition in Renal Cell Carcinoma. Mol Cancer Ther. Apr. 2015; 14(4):1024-34.

Hannigan et al., Integrin-linked kinase: a cancer therapeutic target unique among its ILK. Nat Rev Cancer. Jan. 2005;5(1):51-63.

Hannigan et al., Regulation of cell adhesion and anchorage-dependent growth by a new beta 1-integrin-linked protein kinase. Nature. Jan. 4, 1996;379(6560):91-6.

Hausmann et al., ILKAP, ILK and PINCH1 control cell survival of p53-wildtype glioblastoma cells after irradiation. Oncotarget. Oct. 27, 2015;6(33):34592-605.

Holliday et al., Choosing the right cell line for breast cancer research. Breast Cancer Res. Aug. 12, 2011;13(4):215. 12 pages.

Hsu et al., Function of Integrin-Linked Kinase in Modulating the Stemness of IL-6-Abundant Breast Cancer Cells by Regulating γ-Secretase-Mediated Notch1 Activation in Caveolae. Neoplasia. Jun. 2015;17(6):497-508.

Hsu et al., Integrin-linked kinase as a novel molecular switch of the IL-6-NF-κB signaling loop in breast cancer. Carcinogenesis. Apr. 2016;37(4):430-442.

Hu et al., Differential expressions of integrin-linked kinase, β-parvin and cofilin 1 in high-fat diet induced prostate cancer progression in a transgenic mouse model. Oncol Lett. Oct. 2018;16(4):4945-4952.

Huang et al., Integrin-Linked Kinase Improves Functional Recovery of Diabetic Cystopathy and Mesenchymal Stem Cell Survival and Engraftment in Rats. Can J Diabetes. Jun. 2017;41(3):312-321.

Jantus-Lewintre et al., Analysis of the prognostic value of soluble epidermal growth factor receptor plasma concentration in advanced non-small-cell lung cancer patients. Clin Lung Cancer. Sep. 2011;12(5):320-7.

Jones et al., Integrin-linked kinase regulates the rate of platelet activation and is essential for the formation of stable thrombi. J Thromb Haemost. Aug. 2014;12(8):1342-52.

Kang et al., Integrin-Linked Kinase in Muscle is Necessary for the Development of Insulin Resistance in Diet-Induced Obese Mice. Diabetes. Jun. 2016;65(6):1590-600.

Karachaliou et al., Integrin-linked kinase (ILK) and src homology 2 domain-containing phosphatase 2 (SHP2): Novel targets in EGFR—mutation positive non-small cell lung cancer (NSCLC). EBioMedicine. Jan. 2019;39:207-214.

Kim et al., Chelidonine suppresses migration and invasion of MDA-MB-231 cells by inhibiting formation of the integrin-linked kinase/PINCH/α-parvin complex. Mol Med Rep. Aug. 2015;12(2):2161-8.

Kitagawa et al., Activity-based kinase profiling of approved tyrosine kinase inhibitors. Genes Cells. Feb. 2013;18(2):110-22.

Kudryashova et al., Hippo-Integrin-linked Kinase Cross-Talk Controls Self-Sustaining Proliferation and Survival in Pulmonary Hypertension. Am J Respir Crit Care Med. Oct. 1, 2016;194(7):866-877.

Lee et al., Identification and characterization of a novel integrin-linked kinase inhibitor. J Med Chem. Sep. 22, 2011;54(18):6364-74.

Legate et al., ILK, PINCH and parvin: the tIPP of integrin signalling. Nat Rev Mol Cell Biol. Jan. 2006;7(1):20-31.

Li et al., One-dimensional self-assembly of phenylacetylene macrocycles: effect of peripheral substituents. J Colloid Interface Sci. Apr. 1, 2013;395:99-103.

Lu et al., Integrin-linked kinase expression is elevated in human cardiac hypertrophy and induces hypertrophy in transgenic mice. Circulation. Nov. 21, 2006;114(21):2271-9.

Marotta et al., Characterisation of integrin-linked kinase signalling in sporadic human colon cancer. Br J Cancer. Jun. 2, 2003;88(11):1755-62.

Mongroo et al., Beta-parvin inhibits integrin-linked kinase signaling and is downregulated in breast cancer. Oncogene. Nov. 25, 2004;23(55):8959-70.

Moyer et al., Induction of apoptosis and cell cycle arrest by CP-358,774, an inhibitor of epidermal growth factor receptor tyrosine kinase. Cancer Res. Nov. 1, 1997;57(21):4838-48.

Nishimura et al., A dual role for integrin-linked kinase and β1-integrin in modulating cardiac aging. Aging Cell. Jun. 2014;13(3):431- 40.

Pandey et al., Identification of orally active, potent, and selective 4-piperazinylquinazolines as antagonists of the platelet-derived growth factor receptor tyrosine kinase family. J Med Chem. Aug. 15, 2002;45(17):3772-93.

Pang et al., Tissue Stiffness and Hypoxia Modulate the Integrin-Linked Kinase ILK to Control Breast Cancer Stem-like Cells. Cancer Res. Sep. 15, 2016;76(18):5277-87.

Patricelli et al., In situ kinase profiling reveals functionally relevant properties of native kinases. Chem Biol. Jun. 24, 2011;18(6):699-710.

Pollard et al., Molecular mechanisms controlling actin filament dynamics in nonmuscle cells. Annu Rev Biophys Biomol Struct. 2000;29:545-76.

Qu et al., ILK promotes cell proliferation in breast cancer cells by activating the PI3K/Akt pathway. Mol Med Rep. Oct. 2017;16(4):5036-5042.

Remington's Pharmaceutical Sciences, Mack Publ. Co., Easton, PA. 1985. TOC only. 4 pages.

Schaeffer et al., Tumor expression of integrin-linked kinase (ILK) correlates with the expression of the E-cadherin repressor snail: an immunohistochemical study in ductal pancreatic adenocarcinoma. Virchows Arch. Mar. 2010;456(3):261-8.

Schmidmaier et al., Anti-Adhesion evolves to a promising therapeutic concept in oncology. Curr Med Chem. 2008;15(10):978-90.

Sopko et al., Significance of thymosin β4 and implication of PINCH-1-ILK-α-parvin (PIP) complex in human dilated cardiomyopathy. PLoS One. 2011;6(5):e20184. 10 pages.

Tang et al., The polyelectrolyte nature of F-actin and the mechanism of actin bundle formation. J Biol Chem. Apr. 12, 1996;271(15):8556-63.

Traister et al., ILK induces cardiomyogenesis in the human heart. PLoS One. 2012;7(5):e37802. 14 pages.

Troussard et al., Preferential dependence of breast cancer cells versus normal cells on integrin-linked kinase for protein kinase B/Akt activation and cell survival. Cancer Res. Jan. 1, 2006;66(1):393-403.

Tsoumas et al., ILK Expression in Colorectal Cancer is Associated with EMT, Cancer Stem Cell Markers and Chemoresistance. Cancer Genomics Proteomics. Mar.-Apr. 2018;15(2):127-141.

Vaynberg et al., Non-catalytic signaling by pseudokinase ILK for regulating cell adhesion. Nat Commun. Oct. 26, 2018;9(1):4465. 15 pages.

Verano-Braga et al., SuperQuant-assisted comparative proteome analysis of glioblastoma subpopulations allows for identification of potential novel therapeutic targets and cell markers. Oncotarget. Jan. 25, 2018;9(10):9400-9414.

Williams et al., Integrin-Linked Kinase is Necessary for the Development of Diet-Induced Hepatic Insulin Resistance. Diabetes. Feb. 2017;66(2):325-334.

Wu et al., Integrin-linked kinase regulates smooth muscle differentiation marker gene expression in airway tissue. Am J Physiol Lung Cell Mol Physiol. Dec. 2008;295(6):L988-97.

Yoganathan et al., Integrin-linked kinase (ILK): a "hot" therapeutic target. Biochem Pharmacol. Oct. 15, 2000;60(8):1115-9.

Zeiler et al., Copy number analysis of the murine platelet proteome spanning the complete abundance range. Mol Cell Proteomics. Dec. 2014;13(12):3435-45.

Zhao et al., ILK promotes angiogenic activity of mesenchymal stem cells in multiple myeloma. Oncol Lett. Jul. 2018;16(1):1101-1106.

COMPOUNDS FOR TREATING ILK-MEDIATED DISEASES

The present application is a continuation of U.S. patent application Ser. No. 16/963,968, filed on Jul. 22, 2020, which is a § 371 national entry of PCT/US2019/014500, filed Jan. 22, 2019, which claims priority to U.S. Provisional Application No. 62/621,941, filed on Jan. 25, 2018, each of which is herein incorporated by reference in its entirety.

STATEMENT REGARDING FEDERAL FUNDING

This invention was made with government support under grant number HL058758 awarded by the National Institutes of Health. The government has certain rights in the invention.

FIELD OF THE INVENTION

The present invention relates to compounds that are modulators of Integrin Linked Kinase (ILK), and methods of treating diseases with such compounds. In certain embodiments, the compounds are within Formulas I-VII (e.g., Csbl-1). In some embodiments, the compounds are used to treat an ILK-mediated disease, such as cancer (e.g., triple negative breast cancer) or an inflammatory disease.

BACKGROUND OF THE INVENTION

Breast cancer is the most common cancer for women worldwide, with nearly 1.7 million new cases diagnosed and more than half million deaths in 2012. Clinically, based on the expression levels of estrogen receptor (ER), progesterone receptor (PR), and human epidermal growth factor receptor 2 (HER2), breast cancer is classified into subgroups of hormone receptor-positive, HER-2-positive, and triple-negative breast cancer. Triple-negative breast cancer (TNBC), characterized by the absence of ER/PR and lack of overexpression of HER2, represents approximately 15-20% of all breast cancers.

As TNBC does not respond to either hormonal therapy or anti-HER2 agents, standard chemotherapy is currently the mainstay of systemic medical treatment therefor. TNBC initially responds to conventional chemotherapy, however patients frequently have rapid relapses and currently there is no effective treatment thereafter. In addition, TNBC is more aggressive than other subtypes of breast cancer, which has great propensity to metastasize to the lungs and brain. So patients with TNBC usually have a poor prognosis and a shorter overall survival chance compared with other subtypes of breast cancer.

SUMMARY OF THE INVENTION

The present invention relates to compounds that are modulators of Integrin Linked Kinase (ILK), and methods of treating diseases with such compounds. In certain embodiments, the compounds are within Formulas I-VII (e.g., Csbl-1). In some embodiments, the compounds are used to treat an ILK-mediated disease, such as cancer (e.g., triple negative breast cancer) or an inflammatory disease.

In some embodiments, provided herein are compositions comprising: a compound having a structure of Formula I, or a salt thereof, wherein Formula I is:

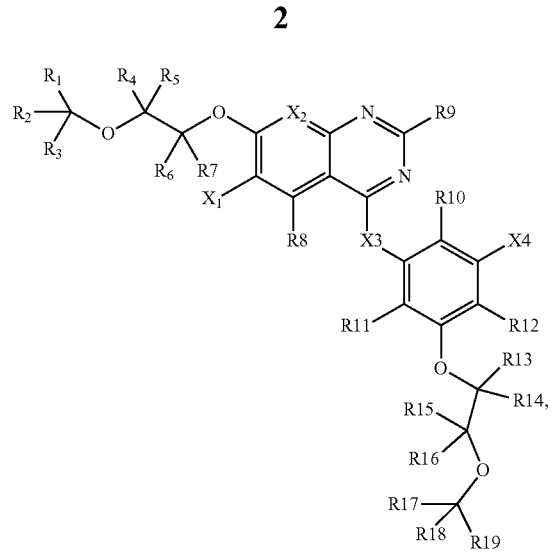

wherein R1-R7, R13-R16, and X1 are each an atom or group independently selected from: hydrogen, deuterium, methyl, trifluoromethyl, lower alkyl, methoxy, lower alkoxy, aryloxy, trifluoromethoxy, —SCF$_3$, cyano, nitro, amino, lower alkylamino, lower dialkylamino, mercapto, lower alkylthio, arylthio, formyl, acetyl, lower alkylcarbonyl, arylcarbonyl, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, aminocarboxy, lower alkylaminocarboxy, arylaminocarboxy, trifluoroacetyl, halogen, hydroxylcarbonyl, lower alkoxylcarbonyl, aryloxycarbonyl, sulfinyl, lower alkylsulfinyl, arylsulfinyl, sulfonyl, lower alkylsulfonyl, arylsulfonyl, sulfonamido, lower alkylsulfonamido, arylsulfonamido, and aryl;

wherein at least one of R1-R7, R14-R19, and X1 is not hydrogen;

wherein R17-R19 are each independently selected from: hydrogen, deuterium, methyl, trifluoromethyl, lower alkyl, methoxy, lower alkoxy, aryloxy, trifluoromethoxy, —SCF$_3$, cyano, nitro, amino, lower alkylamino, lower dialkylamino, mercapto, lower alkylthio, arylthio, acetyl, lower alkylcarbonyl, arylcarbonyl, formyl, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, aminocarboxy, lower alkylaminocarboxy, arylaminocarboxy, trifluoroacetyl, halogen, hydroxylcarbonyl, lower alkoxylcarbonyl, aryloxycarbonyl, sulfinyl, lower alkylsulfinyl, arylsulfinyl, sulfonyl, lower alkylsulfonyl, arylsulfonyl, sulfonamido, lower alkylsulfonamido, arylsulfonamido, aryl, —OH, —CH$_2$—OH, —CH$_2$—NH$_2$, —CH$_2$—NO$_2$, —CH$_2$—COOH, —CH$_2$—CN, and —CH$_2$—CONH$_2$;

wherein R8-R12 are each independently selected from: hydrogen, deuterium, fluorine, chlorine, bromine, and iodine;

wherein X2 is N or CH;

wherein X3 is NH, O, S, or CH$_2$; and wherein X4 is selected from: fluorine, chlorine, bromine, iodine, —CN, and —C≡CY where Y is hydrogen, or deuterium.

In certain embodiments, provided herein are composition comprising: a compound having a structure of Formula II, or a salt thereof, wherein Formula II is:

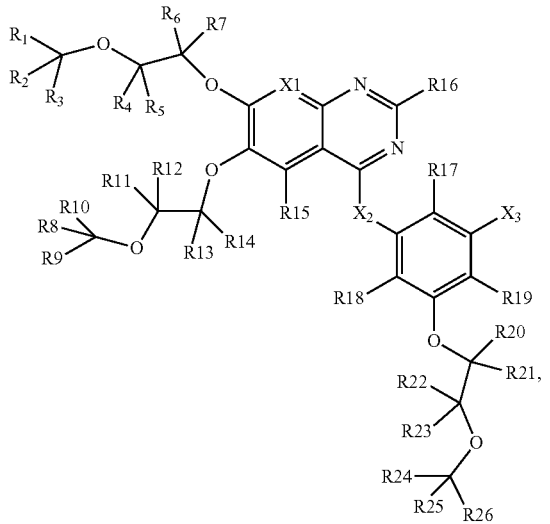

wherein R1-R14, and R20-R23 are each an atom or group independently selected from: hydrogen, deuterium, methyl, lower alkyl, methoxy, lower alkoxy, aryloxy, trifluoromethyl, trifluoromethoxy, —SCF$_3$, cyano, nitro, amino, lower alkylamino, lower dialkylamino, mercapto, lower alkylthio, arylthio, formyl, acetyl, lower alkylcarbonyl, arylcarbonyl, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, aminocarboxy, lower alkylaminocarboxy, arylaminocarboxy, trifluoroacetyl, halogen, hydroxylcarbonyl, lower alkoxylcarbonyl, aryloxycarbonyl, sulfinyl, lower alkylsulfinyl, arylsulfinyl, sulfonyl, lower alkylsulfonyl, arylsulfonyl, sulfonamido, lower alkylsulfonamido, arylsulfonamido, and aryl, and wherein at least one among R1-R14, R21-R26 is not hydrogen;

wherein R24-R26 are each independently selected from: hydrogen, deuterium, methyl, lower alkyl, methoxy, lower alkoxy, aryloxy, trifluoromethyl, trifluoromethoxy, —SCF$_3$, cyano, nitro, amino, lower alkylamino, lower dialkylamino, mercapto, lower alkylthio, arylthio, formyl, acetyl, lower alkylcarbonyl, arylcarbonyl, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, aminocarboxy, lower alkylaminocarboxy, arylaminocarboxy, trifluoroacetyl, halogen, hydroxylcarbonyl, lower alkoxylcarbonyl, aryloxycarbonyl, sulfinyl, lower alkylsulfinyl, arylsulfinyl, sulfonyl, lower alkylsulfonyl, arylsulfonyl, sulfonamido, lower alkylsulfonamido, arylsulfonamido, aryl, —OH, —CH$_2$—OH, —CH$_2$—NH$_2$, —CH$_2$—NO$_2$, —CH$_2$—COOH, —CH$_2$—CN, and —CH$_2$—CONH$_2$;

wherein R15-R19 are each independently selected from: hydrogen, deuterium, fluorine, chlorine, bromine, and iodine;

wherein X1 is nitrogen or CH;
wherein X2 is selected from: NH, O, S, and CH$_2$; and
wherein X3 is selected from: fluorine, chlorine, bromine, iodine, —CN, and —C≡CY where Y is hydrogen or deuterium.

In other embodiments, provided herein are compositions comprising: a compound having a structure of Formula III, or a salt thereof, wherein Formula III is:

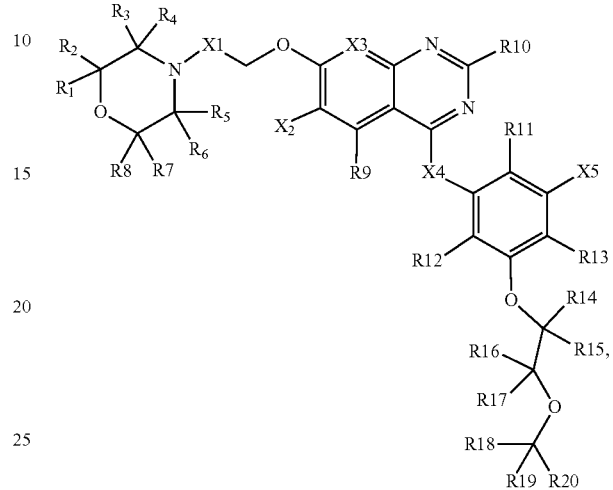

wherein X1 is n-propylene, and wherein 1 to 6 hydrogen atoms are optionally replaced in said n-propylene with deuterium atoms;
wherein X2 is selected from: —OH, —OD, —OCH3, —OCH2D, —OCHD$_2$, and —OCD$_3$, wherein D is deuterium;
wherein X3 is N or CH;
wherein X4 is selected from: NH, O, S, and CH$_2$;
X5 is selected from: fluorine, chlorine, bromine, iodine, —CN, and —C≡CY where Y is hydrogen or deuterium;
wherein R1-R8 are each independently selected from: hydrogen and deuterium;
wherein R9-R13 are each independently selected from: hydrogen, deuterium, fluorine, chlorine, bromine, and iodine;
wherein R14-R17 are each an atom or group independently selected from: hydrogen, deuterium, methyl, lower alkyl, methoxy, lower alkoxy, aryloxy, trifluoromethyl, trifluoromethoxy, —SCF$_3$, cyano, nitro, amino, lower alkylamino, lower dialkylamino, mercapto, lower alkylthio, arylthio, formyl, acetyl, lower alkylcarbonyl, arylcarbonyl, lower alkylcarbonyl, arylcarbonyl, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, aminocarboxy, lower alkylaminocarboxy, arylaminocarboxy, trifluoroacetyl, halogen, hydroxylcarbonyl, lower alkoxylcarbonyl, aryloxycarbonyl, sulfinyl, lower alkylsulfinyl, arylsulfinyl, sulfonyl, lower alkylsulfonyl, arylsulfonyl, sulfonamido, lower alkylsulfonamido, arylsulfonamido, and aryl, wherein at least one among R14-R20 is not hydrogen; and
wherein R18-R20 are each independently selected from: hydrogen, deuterium, methyl, lower alkyl, methoxy, lower alkoxy, aryloxy, trifluoromethyl, trifluoromethoxy, —SCF$_3$, cyano, nitro, amino, lower alkylamino, lower dialkylamino, mercapto, lower alkylthio, arylthio, formyl, acetyl, lower alkylcarbonyl, arylcarbonyl, lower alkylcarbonyl, arylcarbonyl, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, aminocarboxy, lower alkylaminocarboxy, arylaminocarboxy, trifluoroacetyl, halogen, hydroxylcarbonyl, lower alkoxylcarbonyl, aryloxycarbonyl, sulfinyl, lower alkylsulfinyl, arylsulfinyl, sulfonyl, lower alkylsulfonyl, arylsulfonyl, sulfonamido, lower alkylsulfonamido, arylsulfonamido, aryl, —OH, —CH$_2$—OH, —CH$_2$—NH$_2$, —CH$_2$—NO$_2$, —CH$_2$—COOH, —CH$_2$—CN, and —CH$_2$—CONH$_2$.

In some embodiments, provided herein are compositions comprising: a compound having a structure of Formula IV, or a salt thereof, wherein Formula IV is:

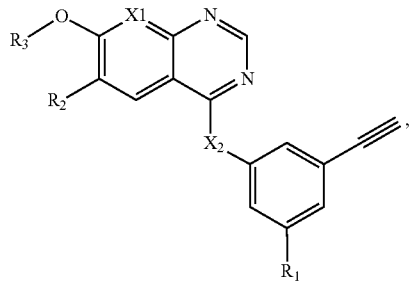

wherein R1 is selected from: 2-methoxyethoxy, 2-ethoxyethoxy, 2-morpholinoethoxy, ethynyl, 2-(2-hydroxyethoxy)ethoxy, —O—CH$_2$CH$_2$CH$_2$OH, —O—CH$_2$CH$_2$—NO$_2$, —O—CH$_2$CH$_2$COOH, —O—CH$_2$CH$_2$—CONH$_2$, —O—CH$_2$CH$_2$—O—CH$_2$OH, —O—CH$_2$CH$_2$—O—CH$_2$CN, —O—CH$_2$CH$_2$—O—CH$_2$NH$_2$, —O—CH$_2$CH$_2$—O—CH$_2$NO$_2$, —O—CH$_2$CH$_2$—O—CH$_2$COOH, —O—CH$_2$CH$_2$—O—CH$_2$CF$_3$, and —O—CH$_2$CH$_2$—O—CH$_2$CONH$_2$;

wherein R2 is selected from: hydrogen, methoxy, or methoxyethoxy;

wherein R3 is selected from: —CH$_3$ and —CH$_2$CH$_2$—O—CH$_3$;

wherein X1 is selected from: N, and CH; and wherein X2 is selected from: NH, O, S, and CH$_2$.

In particular embodiments, provided herein are compositions comprising: a compound having a structure of Formula V, or a salt thereof, wherein Formula V is:

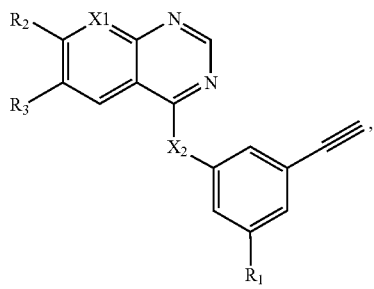

wherein R1 is selected from: 2-methoxyethoxy, 2-ethoxyethoxy, 2-morpholinoethoxy, ethynyl, 2-(2-hydroxyethoxy)ethoxy, —O—CH$_2$CH$_2$CH$_2$OH, —O—CH$_2$CH$_2$—NO$_2$, —O—CH$_2$CH$_2$COOH, —O—CH$_2$CH$_2$—CONH$_2$, —O—CH$_2$CH$_2$—O—CH$_2$OH, —O—CH$_2$CH$_2$—O—CH$_2$CN, —O—CH$_2$CH$_2$—O—CH$_2$NH$_2$, —O—CH$_2$CH$_2$—O—CH$_2$NO$_2$, —O—CH$_2$CH$_2$—O—CH$_2$COOH, —O—CH$_2$CH$_2$—O—CH$_2$CF$_3$, and —O—CH$_2$CH$_2$—O—CH$_2$CONH$_2$;

wherein R2 is selected from: hydrogen, methoxy, and methoxyethoxy;

wherein R3 is selected from: hydrogen, methoxy, and methoxyethoxy;

wherein X1 is N or CH; and wherein X2 is selected from: NH, O, S, and CH$_2$.

In additional embodiments, provided herein are compositions comprising: a compound having a structure of Formula VI, or a salt thereof, wherein Formula VI is:

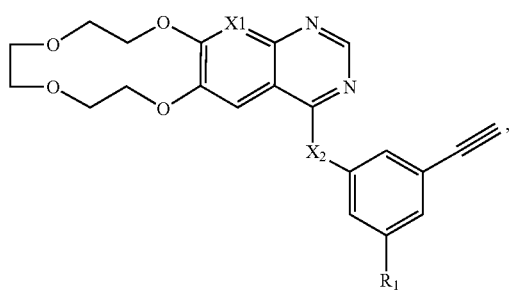

wherein R1 is selected from: 2-methoxyethoxy, 2-ethoxyethoxy, 2-morpholinoethoxy, ethynyl, 2-(2-hydroxyethoxy)ethoxy, —O—CH$_2$CH$_2$CH$_2$OH, —O—CH$_2$CH$_2$—NO$_2$, —O—CH$_2$CH$_2$COOH, —O—CH$_2$CH$_2$—CONH$_2$, —O—CH$_2$CH$_2$—O—CH$_2$OH, —O—CH$_2$CH$_2$—O—CH$_2$CN, —O—CH$_2$CH$_2$—O—CH$_2$NH$_2$, —O—CH$_2$CH$_2$—O—CH$_2$NO$_2$, —O—CH$_2$CH$_2$—O—CH$_2$COOH, —O—CH$_2$CH$_2$—O—CH$_2$CF$_3$, and —O—CH$_2$CH$_2$—O—CH$_2$CONH$_2$;

wherein X1 is N or CH; and wherein X2 is selected from: NH, O, S, and CH$_2$.

In certain embodiments, provided herein are compositions comprising: a compound having a structure of Formula VII, or a salt thereof, wherein Formula VII is:

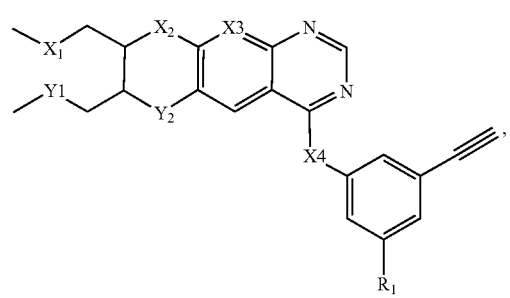

wherein R1 is selected from: 2-methoxyethoxy, 2-ethoxyethoxy, 2-morpholinoethoxy, ethynyl, 2-(2-hydroxyethoxy)ethoxy, —O—CH$_2$CH$_2$CH$_2$OH, —O—CH$_2$CH$_2$—NO$_2$, —O—CH$_2$CH$_2$COOH, —O—CH$_2$CH$_2$—CONH$_2$, —O—CH$_2$CH$_2$—O—CH$_2$OH, —O—CH$_2$CH$_2$—O—CH$_2$CN, —O—CH$_2$CH$_2$—O—CH$_2$NH$_2$, —O—CH$_2$CH$_2$—O—CH$_2$NO$_2$, —O—CH$_2$CH$_2$—O—CH$_2$COOH, —O—CH$_2$CH$_2$—O—CH$_2$CF$_3$, and —O—CH$_2$CH$_2$—O—CH$_2$CONH$_2$;

wherein X1 and Y1 are O; and
wherein X2 and Y2 are each independently O or $CH_2$.

In some embodiments, the compound blocks Mg-ATP binding to human Integrin Linked Kinase (ILK). In other embodiments, the compound modulates ILK-mediated cytoskeleton assembly. In further embodiments, the compound is an anti-cancer agent. In additional embodiments, the compound is an anti-inflammatory compound. In further embodiments, the compound is selected from the group consisting of: Compound 1 (Csbl-1), Compound 3 (cmpd #3), Compound 4 (cmpd #4), Compound 1 new (cmpd #1new), Compound 2 new (cmpd #2new), Compound 7 (cmpd #7), and Compound 8 (Csbl-2).

In particular embodiments, provided herein are methods comprising: treating a subject with any of the compounds described above or herein (e.g., administering or providing the compound to a subject). In particular embodiments, the subject (e.g., human subject) has at least one condition selected from the group consisting of: cancer, diabetes, breast cancer, triple negative breast cancer, solid tumors, an inflammatory disease, ulcerative colitis, psoriasis, scleroderma, systemic lupus erythematosus and atopic dermatitis, and inflammatory arthritis, diabetes, type 2 diabetes, a cardiovascular disease, hypertension, heart attack. In some embodiments, the treating is under conditions such that at least one symptom of said at least one condition is reduced or eliminated. In further embodiments, the subject is a human (e.g., human female or human male). In certain embodiments, the subject has an ILK-mediated disease or condition selected from the group consisting of: cancer (e.g., leukemia, colon cancer, lung cancer, prostate cancer, pancreatic cancer, brain cancer, kidney cancer, breast cancer, skin cancer or myeloma), diabetes, thrombosis, aging, heart disease, and pulmonary disease (e.g., pulmonary hypertension).

In certain embodiments, the compound is co-administered with an anti-cancer agent and/or an anti-inflammatory agent. In particular embodiments, the subject is selected from the group consisting of: i) a subject having a disease, ii) a subject displaying signs or symptoms or pathology indicative of said disease, iii) a subject suspected of having said disease, iv) a subject suspected of displaying signs or symptoms or pathology indicative of said disease, v) a subject at risk of said disease, vi) a subject at risk of displaying pathology indicative of said disease, vii) an animal model of said disease, and viii) a healthy subject wishing to reduce risk of said disease.

In particular embodiments, the treating comprises administering between 0.05 mg-3000 mg of said compound (e.g., daily) to said subject (e.g., 0.05 . . . 1.0 . . . 150 . . . 500 . . . 2000 . . . or 3000 mg). In further embodiments, the treating comprises administering between 25 mg-600 mg of said compound (e.g., daily) to said subject (e.g., 25 . . . 100 . . . 300 . . . 400 . . . 600 mg). In some embodiments, the treating comprises administering 25 mg-600 mg to said subject per day for at least two days (e.g., for at least 2 . . . 14 . . . 28 . . . 150 . . . or 360 days).

DESCRIPTION OF THE DRAWINGS

The patent or application file contains at least one drawing executed in color. Copies of this patent or patent application publication with color drawings will be provided by the Office upon request and payment of the necessary fee.

DEFINITIONS

Figure 1:
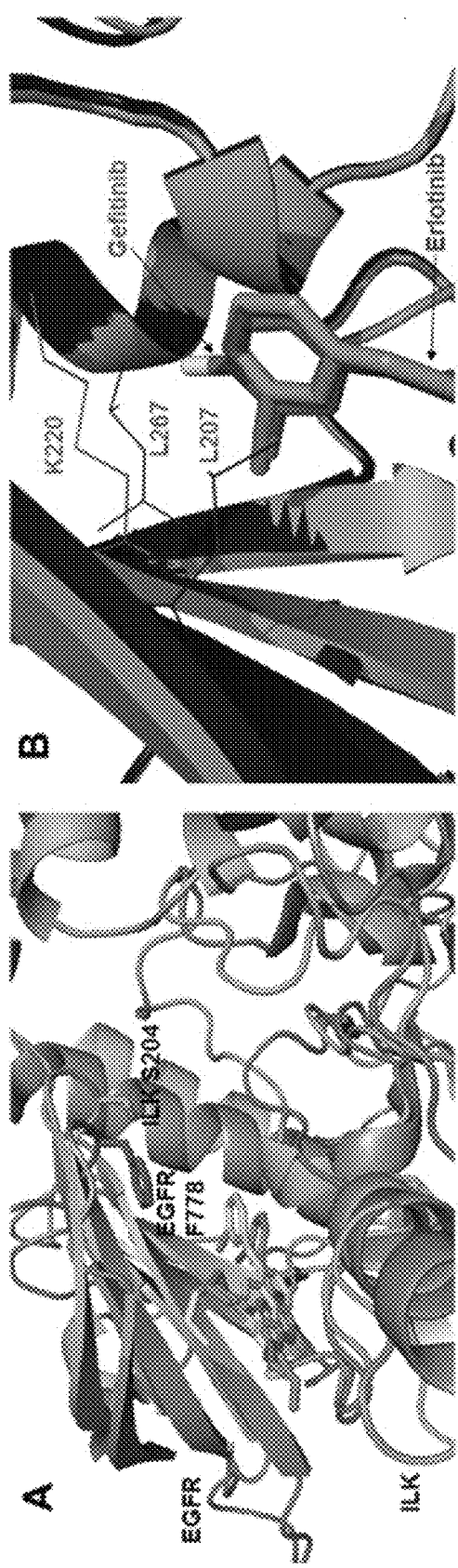
FIG. 1, panels A and B, show a hypothetical structural comparison of the drug binding modes for ILK and EGFR. (A) Structural comparison of ILK (cyan)-erlotinib (green) and EGFR (brown)-erlotinib (yellow) complexes showing the similar drug binding modes with different surrounding residues such as EGFR F778 vs ILK S204. (B) Structural comparison of ILK (green)-erlotinib (orange) complex with ILK (blue)-gefitinib (pink) complex showing that the surrounding L207, K220 (hydrophobic part), and L267 interact differently with erlotinib and gefitinib.

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the terms "administration," and "administering," refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising a compound of Formula I-VII, and one or more other agents—e.g., an anti-cancer or anti-inflammatory agent). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the term "pharmaceutical composition" refers to the combination of an active agent (e.g., composition comprising a compound of Formulas I-VII) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention (e.g., in Formulas I-VII) that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

DETAILED DESCRIPTION OF THE INVENTION

The present invention relates to compounds that are modulators of Integrin Linked Kinase (ILK), and methods of treating diseases with such compounds. In certain embodiments, the compounds are within Formulas I-VII (e.g., Csbl-1). In some embodiments, the compounds are used to treat an ILK-mediated disease, such as cancer (e.g., triple negative breast cancer) or an inflammatory disease.

Work conducted during the development of embodiments described herein employed a structure-based rational design to design and synthesize a series of small molecule inhibitors to specifically block the Mg-ATP binding to ILK—a distinct pseudokinase essential for controlling cytoskeleton-dependent cell adhesion and survival in many physiological and pathological processes. One compound that was synthesized Csbl-1 (Compound 1) was found to inhibit growth of triple negative breast cancer (TNBC) cells and tumors where ILK is highly elevated with no apparent toxicity to healthy breast cells and mice under the same experimental conditions. Compounds provided herein are ILK inhibitors that are specific for ILK but with little effect to (e.g., do not bind to) EGFR and other structurally similar kinases, and therefore could be less toxic and have a potential to reduce side effects in disease treatment.

ILK is a central component of focal adhesions, supramolecular complexes that link extracellular matrix to actin filaments, regulating cytoskeleton organization and diverse cytoskeleton-dependent cellular responses such as cell adhesion, cell shape change, migration, proliferation, and survival (Legate et al., 2006). Being critically involved in the progression of cancer, diabetes, kidney failure, inflammation, and cardiovascular diseases, ILK has been widely recognized as a therapeutic target (Yoganathan et al., 2002; Hannigan et al., 2005; Schmidmaier and Baumann, 2008; Durbin et al., 2009; Cabodi et al., 2010). However, being originally thought to function as a kinase (Hannigan et al., 1996), ILK was later found to contain an unusual pseudoactive site incapable of performing catalysis (Fukuda et al., 2009, 2011), precluding the conventional kinase activity-based drug development. Interestingly, despite lacking kinase activity, it was discovered that ILK still binds Mg-ATP at the pseudoactive site (Fukuda et al., 2009, 2011) and is capable of utilizing the bound MgATP to transduce non-catalytic signals for modulating cytoskeleton and cell adhesion dynamics (Vaynberg et al., 2018). Given that ILK is highly upregulated in many disease states (Yoganathan et al., 2002; Hannigan et al., 2005; Schmidmaier and Baumann, 2008; Durbin et al., 2009; Cabodi et al., 2010), the compounds provided herein are useful for targeting ILK, yet in conceptually different way, i.e., rather than inhibiting the non-existent ILK kinase activity, the compounds may be used to block the MgATP binding to ILK and inhibit the relevant pathway(s) and dysfunctional cellular processes in various diseases. Since ILK has no isoform and is highly concentrated especially in cell adhesion sites, the compounds herein could be highly effective in treating ILK-mediated diseases.

Currently there is no proven targeted therapy for triple negative breast cancer. Furthermore, because ILK has no isoform, ILK specific compounds herein (e.g., Csbl-1) may have minimal side effects on treating diseases where ILK is elevated, as compared to many known drugs such as erlotinib and gefitinib that target EGFR as well as homologs and structurally similar kinases (Kitagawa et al., 2013).

The present invention provides pharmaceutical compositions which may comprise one or more forms of a compound of Formula I-VII (e.g., Compound 1), alone or in combination with at least one other agent, such as a stabilizing compound, or a chemotherapeutic drug, and may be administered in any sterile, biocompatible pharmaceutical carrier, including, but not limited to, saline, buffered saline, dextrose, and water.

The methods of the present invention find use in treating (e.g., prophylactically or therapeutically) ILK-mediated diseases. A compound of Formula I-VII (e.g., Compound 1) can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present invention, compositions and/or formulations comprising a compound of Formula I-VII can be administered to a subject alone, or in combination with other forms of a compound of Formula I-VII, drugs, small molecules, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions comprising a compound of Formula I-VII may be administered alone to individuals subject to or suffering from a disease or condition (e.g., breast cancer or an inflammatory disease). Compositions comprising a compound of Formula I-VII may be added to a nutritional drink or food (e.g., ENSURE, POWERBAR, or the like), a multivitamin, nutritional products, food products, etc. for daily consumption.

Depending on the target sought to be altered by treatment, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of the pharmaceutical agent may be that amount that alters the expression of a specific gene. Determination of effective amounts is well within the capability of those skilled in the art, especially in light of the disclosure provided herein. In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes). Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For compositions or formulations comprising a compound of Formula I-VII, conditions indicated on the label may include treatment of condition related to prophylactic or therapeutic treatment of cancer or an inflammatory disease.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range. A therapeutically effective dose refers to that amount of which ameliorates or prevents symptoms of a disease state or condition (e.g., through altering gene expression) Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation. In some embodiments, a compound of Formula I-VII is administered at a daily dose of between 25-600 mg per day (e.g., administered to a subject in such a way so as to provide between 25-600 mg of a compound of Formula I-VII to the subject each day). Doses outside of 25-600 mg may be used. In some embodiments, a single dose of a compound of Formula I-VII is administered once daily. In other embodiments, 2, 3, 4, or more doses may be administered each day (e.g., once in the morning and once at night, or once every 4 to 6 hours). For example, in some embodiments, a compound of Formula I-VII is administered to a subject in three separate, more than three separate, two separate, or less than two separate doses. In some embodiments, the daily dose is administered in a time release capsule.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical compositions of the present invention include, but are not limited to, solutions, emulsions, and liposome-containing formulations.

These compositions may be generated from a variety of components that include, but are not limited to, preformed liquids, self-emulsifying solids and self-emulsifying semi-solids. The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Thus, in some embodiments, the compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation. In some embodiments, the invention provides pharmaceutical compositions containing (a) one or more forms of a compound of Formula I-VII and (b) one or more other agents (e.g., anti-cancer therapeutic).

The present invention also includes methods involving co-administration of compounds comprising a compound of Formula I-VII described herein with one or more additional active agents. Indeed, it is a further aspect of this invention to provide methods for enhancing prior art therapies and/or pharmaceutical compositions by co-administering a composition comprising a compound of Formula I-VII of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations.

In certain embodiments, the compounds described herein are administered to a subject with an ILK-mediated disease or condition. Examples of such diseases and conditions include, but are not limited to, such diseases and conditions described in the literature. One example of such a disease is cancer, including, but not limited to, leukemia (see, e.g., de la Puente et al., Leuk Res. 2015 Sep. 9. pii: S0145-2126 (15)30377-5, herein incorporated by reference), colon cancer (see, e.g., Tsoumas et al., Cancer Genomics Proteomics. 2018 March-April; 15(2):127-141; and Bravou et al., J Pathol. 2006 January; 208(1):91-9; and Marotta et al., Br J Cancer. 2003 Jun. 2; 88(11):1755-62; all of which are herein incorporated by reference), lung cancer (see, e.g., Karachaliou et al., EBioMedicine, 2018 Nov. 22. pii: S2352-3964(18)30541-3, herein incorporated by reference), prostate cancer (see, e.g., Hu et al., Oncol Lett. 2018 October; 16(4):4945-4952, herein incorporated by reference), pancreatic cancer (see, e.g., Schaeffer et al., Virchows Arch. 2010 March; 456(3):261-8, herein incorporated by reference), kidney cancer (see, e.g., Han et al., Mol Cancer Ther. 2015 April; 14(4):1024-34; and Agouni et al., Carcinogenesis. 2007 September; 28(9):1893-901; both of which are herein incorporated by reference); glioblastoma cancer (see, e.g., Hausmann et al., Oncotarget. 2015 Oct. 27; 6(33):34592-605; and Verano-Braga et al., Oncotarget. 2018 Jan. 25; 9(10):9400-9414; both of which are herein incorporated by reference); breast cancer (see, e.g., Qu et al., Mol Med Rep. 2017 October; 16(4):5036-5042; and Pang et al., Cancer Res. 2016 Sep. 15; 76(18):5277-87; both of which are herein incorporated by reference); myeloma (see, e.g., Zhao et al., Oncol Lett. 2018 July; 16(1):1101-1106; herein incorporated by reference), and skin cancer (see, e.g., Dai et al., Clin. Cancer Res. 2003 Oct. 1; 9(12):4409-14 (herein incorporated by reference). Other examples of such a diseases and conditions include, but are not limited to, diabetes (see, e.g., Huang et al., Can J Diabetes. 2017 June; 41(3):312-321; Williams et al., Diabetes. 2017 February; 66(2):325-334; and Kang et al., Diabetes. 2016 June; 65(6):1590-600; all of which are herein incorporated by reference), thrombosis (see, e.g., Jones et al., J Thromb Haemost. 2014 August; 12(8):1342-52, herein incorporated by reference), aging (see, e.g., Nishimura et al., Aging Cell. 2014 June; 13(3): 431-40; herein incorporated by reference), heart diseases (e.g., Traister et al., PLoS One. 2012; 7(5):e37802; Sopko et al., PLoS One. 2011; 6(5):e20184; and Lu et al., Circulation. 2006 Nov. 21; 114(21):2271-9; all of which are herein incorporated by reference), pulmonary disease (see, e.g., Wu et al., Am J Physiol Lung Cell Mol Physiol. 2008 December;

295(6):L988-97; and Kudryashova et al., Am J Respir Crit Care Med. 2016 Oct. 1; 194(7):866-877; both of which are herein incorporated by reference).

EXPERIMENTAL

The following examples are provided in order to demonstrate and further illustrate certain preferred embodiments and aspects of the present invention and are not to be construed as limiting the scope thereof.

Example 1

Ilk Inhibitor Development and Characterization

This Example describes the development and characterization of ILK inhibitors.

Development and Biochemical Characterization of Novel ILK Inhibitors

To develop a specific ILK inhibitor, we performed computer-aided docking-based virtual screening on the Mg-ATP-bound pseudoactive site of ILK against a public database (NCI Plated 2007 and NCI Diversity 3) containing ~0.1 million drug-like molecules. However, none of the compounds ranked on the top list showed any detectable binding to purified ILK using fluorescence-based method. We then examined several known ILK inhibitors, which include QLT-0267 (Troussard et al., 2006), compound 22 or T315 (Lee et al., 2011), chelidonine (Kim et al., 2015), which were identified by cell-based assays. Surprisingly, these compounds also had no detectable binding to purified ILK despite previously suggested activity.

Thus, while these compounds were extensively used in studying ILK-mediated cellular and disease processes, their reported inhibitory effects are probably due to unknown artifacts or indirect binding events. Next, we turned our attention to previously reported studies on kinase profiling and quantitative chemical proteomics (Conradt et al., 2011; Patricelli et al., 2011; Augustin et al., 2013). These studies suggested that a widely known lung cancer drug erlotinib, which targets EGFR, might also bind to ILK as an off-target (Conradt et al., 2011; Patricelli et al., 2011; Augustin et al., 2013). By performing a robust fluorescence-based binding assay, we found that the FDA approved drug Erlotinib (TARCEVA) indeed binds potently to purified recombinant ILK at $K_D$~0.43 µM, which is very close to the affinity of Erlotinib to EGFR measured at the same experimental conditions ($K_D$~0.31 µM) (Table 1). Another erlotinib-like EGFR inhibitor Gefitinib exhibited 10-fold weaker binding affinity to ILK ($K_D$~4.51 µM) yet ~3-fold stronger affinity to EGFR ($K_D$~0.11 µM) than erlotinib (Table 1). To understand the structural basis of the erlotinib/gefitinib binding to ILK, we determined high resolution crystal structures of erlotinib/ILK and gefitinib/ILK complexes, which revealed similar drug binding modes but with erlotinib having more hydrophobic contacts to ILK than gefitinib, explaining the reason behind strong binding of erlotinib to ILK compared to gefitinib (FIG. 1 panel B).

The findings above have propelled us to explore the possibility of developing specific ILK inhibitors using the high-resolution structure of erlotinib/ILK complex vs known EGFR/erlotinib structure (PDB code 1M17). Our rationale was to use these structures to guide the design of a novel and selective compound that favors ILK but disfavors EGFR. Detailed structural comparison between the erlotinib/ILK complex and the erlotinib/EGFR complex (FIG. 1 panel A) revealed unique features of the former, which allowed us to design numerous compounds (Table 1) that have been subjected to binding studies. Of these compounds, Csbl-1 (Compound 1) binds to the pseudoactive site of ILK but unfavorably to EGFR (Table 1).

TABLE 1

| Name | Structure | Binding Experiment | ILK - Binding affinity (nM) | EGFR - Binding affinity (nM) | Binding Difference ILK (Kd)/EGFR (Kd) |
|---|---|---|---|---|---|
| Erlotinib | 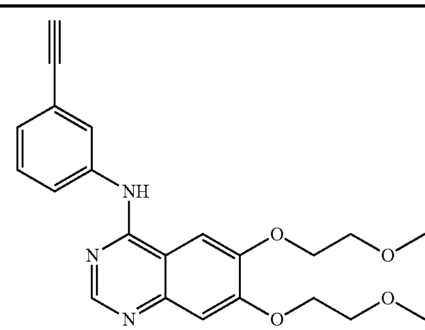 | EnSpire fluorescence intensity | 430 +/- 50 | 310 +/- 30 | 1.3870968 |
| Gefitinib | 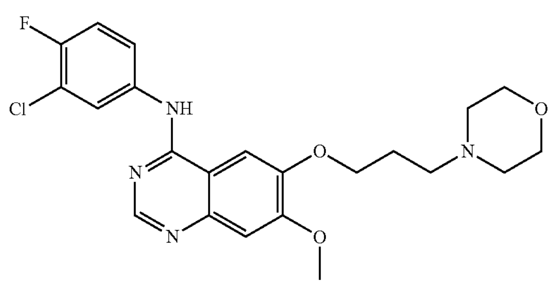 [SMILES: COc1cc2ncnc(Nc3ccc(F)c(Cl)c3)c2cc1OCCCN1CCOCC1] | EnSpire fluorescence intensity | 4510 +/- 720 | 110 +/- 10 | 41 |

TABLE 1-continued

| Name | Structure | Binding Experiment | ILK - Binding affinity (nM) | EGFR - Binding affinity (nM) | Binding Difference ILK (Kd)/EGFR (Kd) |
| --- | --- | --- | --- | --- | --- |
| Erlotinib-4-methylphenyl analog (E4ME) | 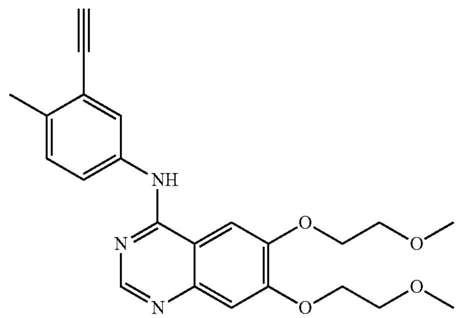 | EnSpire fluorescence intensity | 1546 +/− 222 | 745 +/− 74.8 | 2.075168 |
| Compound 1 (Csbl-1) | 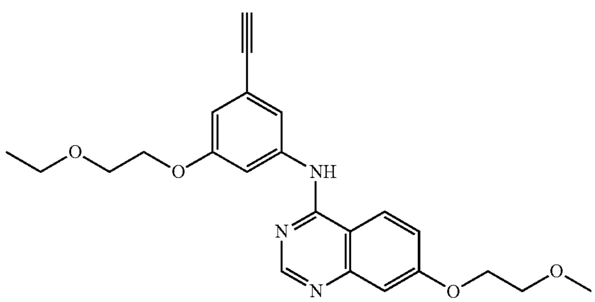 [SMILES: C#Cc1cc(Nc2ncnc3cc(OCCOC)ccc23)cc(OCCOCC)c1] | EnSpire fluorescence intensity | 2770 +/− 290 | 17,700 +/− 1700 | 0.156497 |
| Compound 3 (cmpd#3) | 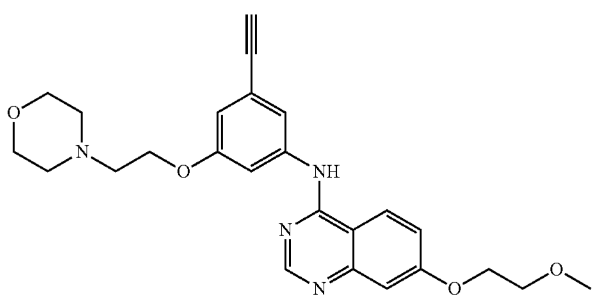 [SMILES: C#Cc1cc(Nc2ncnc3cc(OCCOC)ccc23)cc(OCCN2CCOCC2)c1] | EnSpire fluorescence intensity | 49,570 +/− 2210 | N/A | N/A |
| Compound 4 (cmpd#4) | 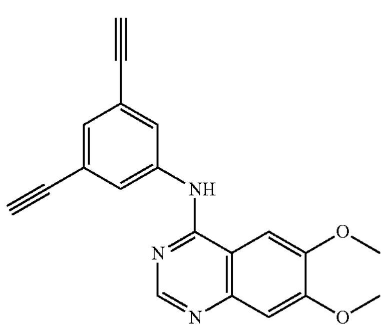 [SMILES: C#Cc1cc(C#C)cc(Nc2ncnc3cc(OC)c(OC)cc23)c1] | EnSpire fluorescence intensity | 1545 +/− 176 | 1153 +/− 161.4 | 1.3399827 |

TABLE 1-continued

| Name | Structure | Binding Experiment | ILK - Binding affinity (nM) | EGFR - Binding affinity (nM) | Binding Difference ILK (Kd)/EGFR (Kd) |
|---|---|---|---|---|---|
| Compound 1 New (cmpd#1new) | 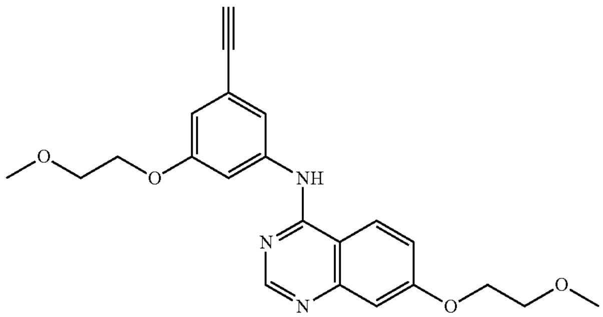 | Nano-temper | 6852.8 +/- 607.27 | 12,658 +/- 1970.9 | 0.5413809 |
| Compound 2 New (cmpd#2new) | 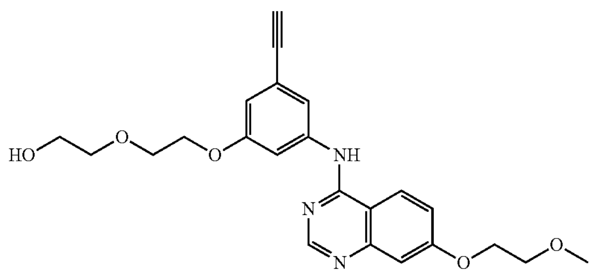 [SMILES: C#Cc1cc(Nc2ncnc3cc(OCCOC)ccc23)cc(OCCOCCO)c1] | Nano-temper | 7995 +/- 527 | N/A | N/A |
| Compound 7 (cmpd #7) | 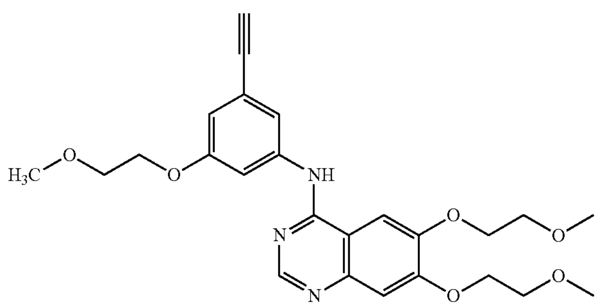 | Nano-temper | 2444.6 +/- 149.08 | 6588.4 +/- 464.84 | 0.371046 |
| Compound 8 (Csbl-2) | 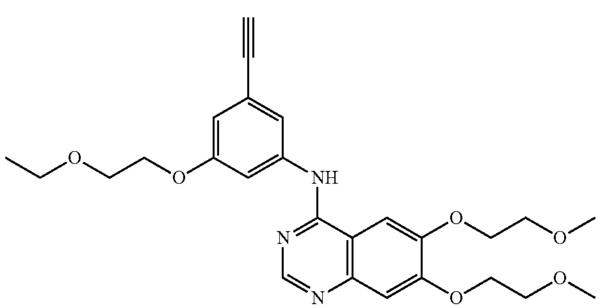 [SMILES: C#Cc1cc(Nc2ncnc3cc(OCCOC)c(OCCOC)cc23)cc(OCCOCC)c1] | Nano-temper | 922.12 +/- 49.959 | 8840 +/- 671 | 0.104312 |

TABLE 1-continued

| Name | Structure | Binding Experiment | ILK - Binding affinity (nM) | EGFR - Binding affinity (nM) | Binding Difference ILK (Kd)/EGFR (Kd) |
|---|---|---|---|---|---|
| Compound 22 | 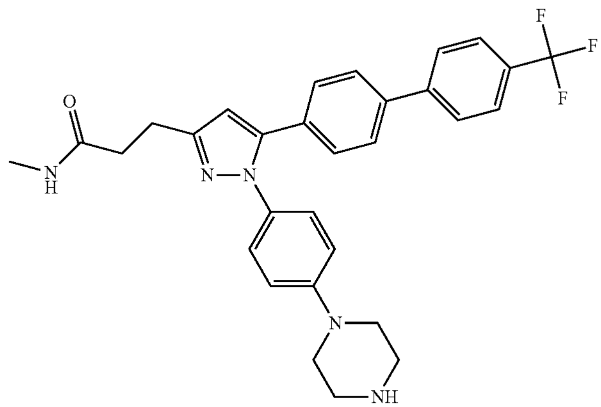 [SMILES: CNC(=O)CCc1cc(-c2ccc(-c3ccc(C(F)(F)F)cc3)cc2)n(-c2ccc(N3CCNCC3)cc2)n1] | EnSpire fluorescence intensity | N/D | N/D | N/D |
| QLT0267-like compound (QLT0267) | 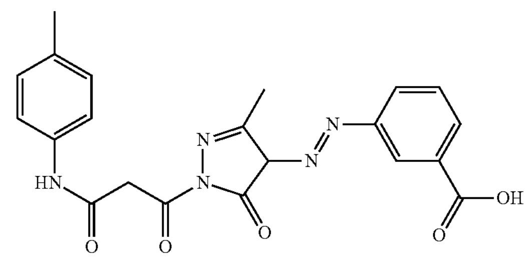 [SMILES: CC1=NN(C(=O)CC(=O)Nc2ccc(C)cc2)C(=O)C1/N=N/c1cccc(C(=O)O)c1] | EnSpire fluorescence intensity | N/D | N/D | N/D |
| Chelidonine | 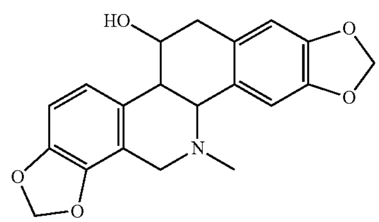 [SMILES: CN1Cc2c(ccc3c2OCO3)C2C(O)Cc3cc4c(cc3C21)OCO4] | EnSpire fluorescence intensity | N/D | N/D | N/D |

Csbl-1 retains quinazoline feature of erlotinib but is chemically distinct with totally different structure (Table 1). The compound is also totally different from previously reported ILK inhibitors that did not bind to purified ILK in our experiments (see Table 1).

To experimentally verify the effectiveness of our design, we synthesized Csbl-1 (Compound 1) and performed the affinity measurement. As expected, Csbl-1 binds potently to ILK at $K_D \sim 2.77$ μM(Table 1) yet unfavorably to EGFR with an affinity that is too weak to be accurately determined under the same experimental condition. Consistently, Csbl-1 has a dramatically reduced $IC_{50}$ (77.2 μM) to EGFR vs erlotinib (1.5 μM) (>50 times reduction). Thus, being potent to bind ILK, Csbl-1 is expected to exert minimal effect on EGFR (e.g., when properly dosed). We also designed Csbl-2 (Compound 8), a Csbl-1 variant, which binds ~3-fold tighter to ILK ($K_D \sim 0.92$ μM(Table 1) than Csbl-1 to ILK ($K_D \sim 2.77$ μM) (Table 1). However, Csbl-2 still binds to EGFR at the $K_D \sim 8.84$ μM. In other words, while Csbl-2 has stronger affinity to ILK than Csbl-1, Csbl-2 might exhibit stronger off-target effect to EGFR than Csbl-1 depending on the drug dosage and disease conditions.

It is important to note here that drug binding affinity or $IC_{50}$ may vary significantly depending on the measurement methods and experimental conditions. For example, the $IC_{50}$ for erlotinib to inhibit purified EGFR is 1.51 μM in our kinase assay using purified EGFR, which is 75 times lower than the previously reported $IC_{50}$-20 nM based on a cell-based assay (Moyer et al., 1997). Thus, comparison of the binding affinities or $IC_{50}$ is only meaningful under the same experimental conditions. Under the same experimental conditions, the affinity of Csbl-1 to ILK ($K_D \sim 2.77$ μM) is ~6 times weaker than that of erlotinib to ILK ($K_D \sim 0.43$ μM) (Table 1). However, Csbl-1 is much more selective to ILK than erlotinib with the latter almost having no selectivity to ILK and EGFR (Table 1). Furthermore, since ILK is extremely abundant in cells (~20 μM, ~12% of actin in non-muscle cells) (Pollard et al., 2000; Zeiler et al., 2014) and its local concentration, e.g., in FAs, is even much higher (likely >submM), it is proposed that Csbl-1 would be quite potent and selective to inhibit the ILK pathway(s) in cells or in disease conditions where ILK level is further elevated. By contrast, EGFR, which has extremely low level even in cancer patients (<35 nM) (Jantus-Lewintre et al., 2011), is expected to be generally insensitive to this inhibitor.

Example 2

Characterization of Csbl-1

This Example describes further characterization of Csbl-1 (Compound 1).

Figure 2:
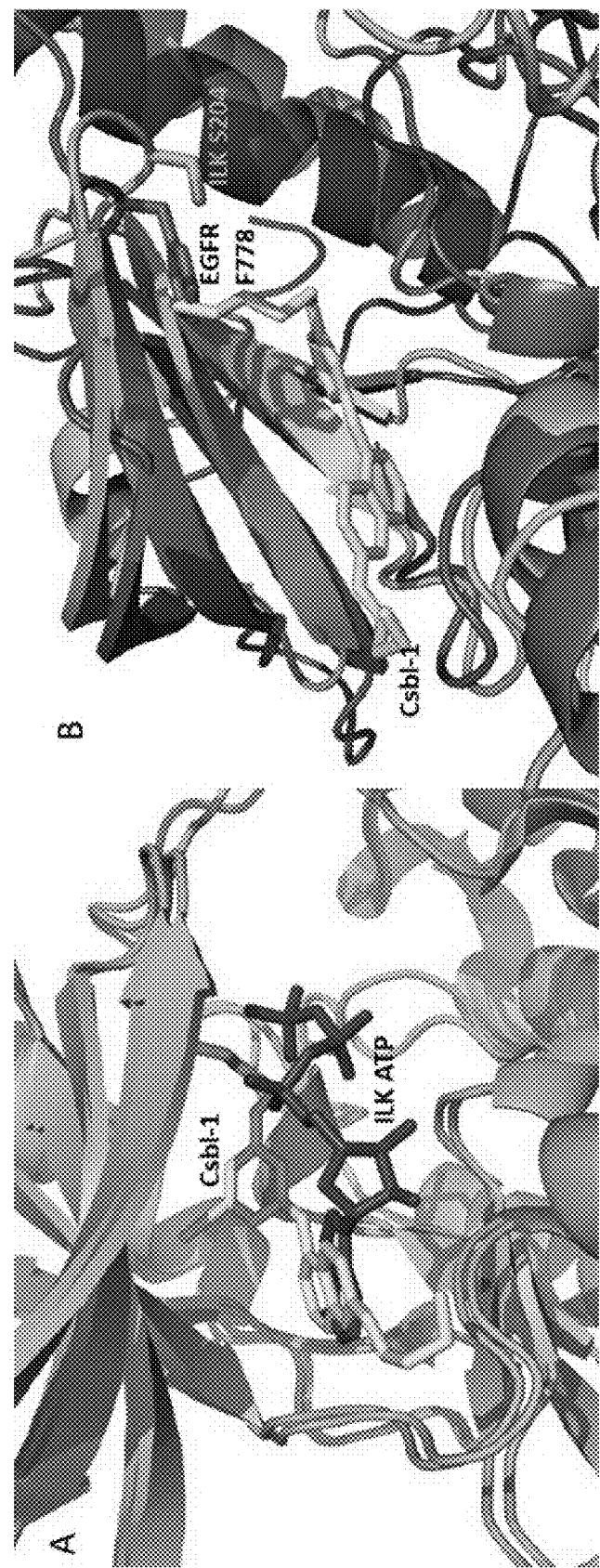
FIG. 2, panels A and B, show hypothetical binding of Csbl-1 (compound 1) to ILK. Panel A shows the crystal structures of ILK bound to ATP (red) and Csbl-1 (yellow) showing that Csbl-1 sterically occludes ATP. Panel B shows a structural comparison of ILK bound to Csbl-1 with EGFR showing that Csbl-1 would exert steric clashes with EGFR such as F778 in the EGFR Gly-rich loop region, whereas the corresponding position is much smaller sized S204 in ILK.
Figure 3:
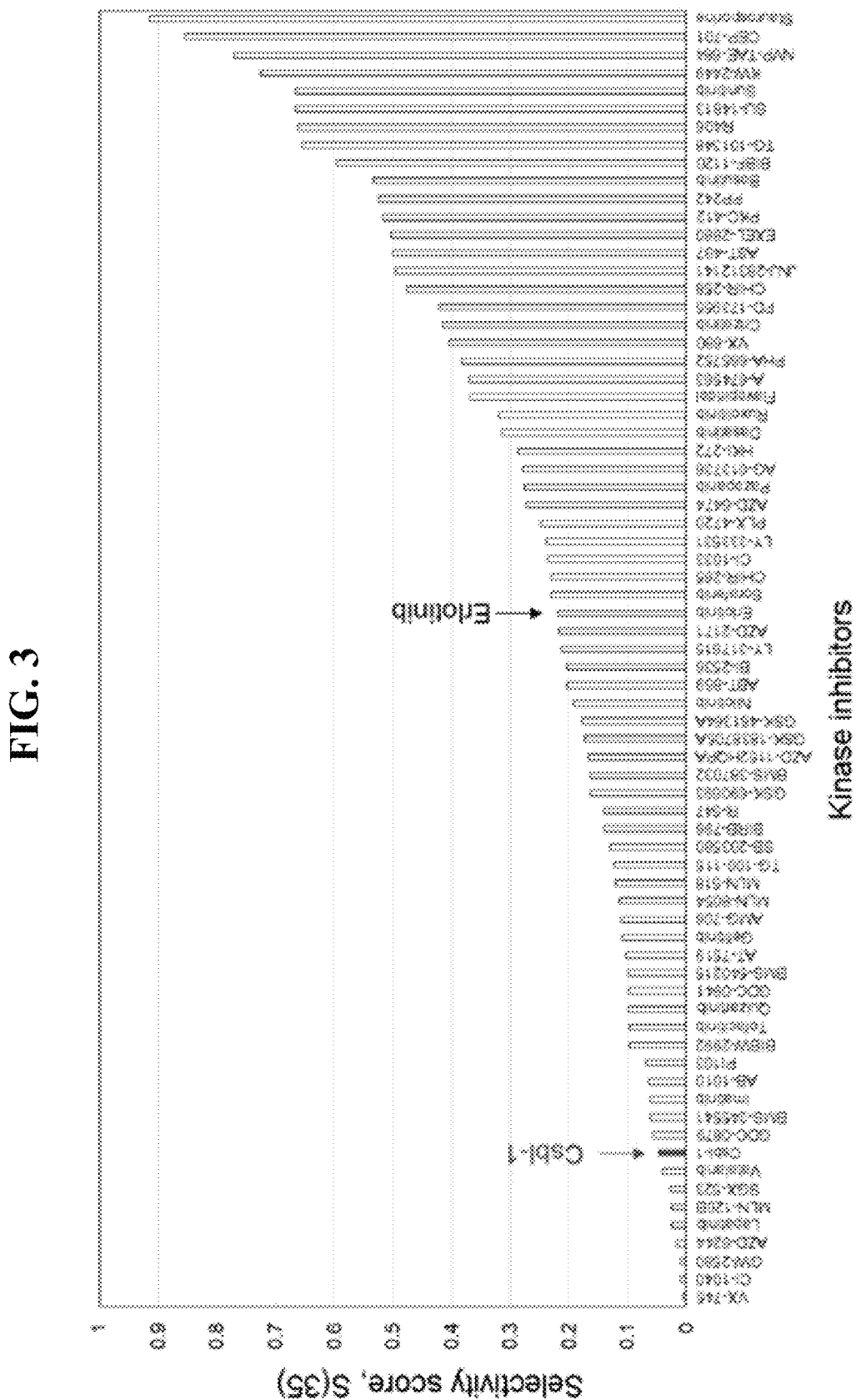
FIG. 3 shows the off target analysis of Csbl-1 vs known kinase inhibitors. Higher selectivity score means stronger off target effects.

Crystal Structure of Csbl-1 Bound to ILK Reveals a Basis for the Inhibitor Specificity To elucidate definitively how Csbl-1 specifically binds to ILK, we determined the crystal structure of Csbl-1/ILK complex. FIG. 2 panel A shows that the Csbl-1 binding would clearly occlude the Mg-ATP binding to ILK. Superposition of Csbl-1/ILK and erlotinib/EGFR structures further reveals that Csbl-1 would indeed have unfavorable binding to active EGFR, e.g., exerting steric clashes with a conserved bulky F778 in Gly rich P loop (corresponding to S204 in ILK) (FIG. 2 panel B). Thus our structure provides a hypothetical atomic basis for understanding why Csbl-1 binds selectively to ILK but unfavorably to EGFR (Table 1). A comprehensive kinase inhibitor off-target analysis suggested that erlotinib may bind more than a dozen of off target kinases with >60% inhibition efficiency (Kitagawa et al., 2013). Analysis of the crystal structures of these kinases or their homologs reveals that they share most of the key structural features such as activation loop configuration and conserved bulky Phe in the Gly rich P loop as seen in active EGFR, which will cause similar steric clashes with Csbl-1. Thus, Csbl-1 is highly selective to ILK pseudoactive site that is distinct from these EGFR-like kinases. Consistently, a proteomic analysis of Csbl-1 against all known FDA-approved kinase inhibitors revealed that Csbl-1 has minimal off-target effect to kinases (FIG. 3). Csbl-1 (compound 1) also exhibits excellent pharmacological ADME (Absorption, Distribution, Metabolism, and Excretion) properties such as toxicity, plasma stability, etc. as shown in Tables 2-12 below.

TABLE 2

Permeability Results of Test Compounds in Caco2 Cell Line

| Compound ID | $P_{app(A-B)}$ ($10^{-6}$, cm/s) | $P_{app(B-A)}$ ($10^{-6}$, cm/s) | Efflux Ratio | Recovery (%)AP-BL | Recovery (%)BL-AP |
|---|---|---|---|---|---|
| Propranolol | 19.46 | 15.88 | 0.82 | 60.83 | 80.03 |
| Digoxin | 0.61 | 16.59 | 27.01 | 87.87 | 96.54 |
| Prazosin | 12.46 | 30.09 | 2.41 | 85.14 | 99.05 |
| Compound 1 | 15.38 | 7.31 | 0.48 | 50.97 | 53.50 |

TABLE 3

The Assessment of Caco2 Cell Monolayer Integrity

| Compound ID | $TEER_{A-B}$ ($\Omega \cdot cm^2$) | $TEER_{B-A}$ ($\Omega \cdot cm^2$) | LY Leakage$_{A-B}$ (%) | LY Leakage$_{B-A}$ (%) |
|---|---|---|---|---|
| Propranolol | 353 | 349 | 0.32 | 0.29 |
| Digoxin | 520 | 484 | 0.23 | 0.20 |
| Prazosin | 551 | 556 | 0.17 | 0.26 |
| Compound 1 | 529 | 547 | 0.24 | 0.18 |

TABLE 4

Stability results of Test Compound and control compound in PBS at pH 7.4 and SIF

| Compound | PH Value | \multicolumn{6}{c}{Remaining Percentage (%)} | | | | | |
|---|---|---|---|---|---|---|---|

| Compound | PH Value | 0 min | 30 min | 60 min | 120 min | 180 min | 240 min |
|---|---|---|---|---|---|---|---|
| Chlorambucil | 7.4 | 100.00 | 37.17 | 11.53 | 2.35 | 0.09 | 0.03 |
| Compound 1 | 7.4 | 100.00 | 102.02 | 105.41 | 103.04 | 104.93 | 99.54 |
| Chlorambucil | SIF | 100.00 | 58.85 | 33.12 | 8.26 | 2.57 | 0.79 |
| Compound 1 | SIF | 100.00 | 104.86 | 109.34 | 105.85 | 108.93 | 109.26 |

TABLE 5

Inhibition of 9 CYP Isoforms by Test Compounds in Human Liver Microsomes

| Compound ID | $IC_{50}$ (μM) | | | | | | | | |
|---|---|---|---|---|---|---|---|---|---|
| | 1A2 | 2A6 | 2B6 | 2C8 | 2C9 | 2C19 | 2D6 | 2E1 | 3A4-M |
| Furafylline | 2.19 | — | — | — | — | — | — | — | — |
| Tranylcypromine | — | 0.69 | — | — | — | — | — | — | — |
| Sulfaphenazole | — | — | — | — | 0.66 | — | — | — | — |
| N-3-benzylnirvanol | — | — | — | — | — | 0.25 | — | — | — |
| Quinidine | — | — | — | 3.72 | — | — | 0.11 | — | — |
| Ketoconazole | — | — | 1.46 | — | — | — | — | — | 0.018 |
| Quercetin | — | — | — | — | — | — | — | — | — |
| Disulfiram | — | — | — | — | — | — | — | 37.71 | — |
| Compound 1 | 33.29 | >50 | >50 | 3.24 | 13.82 | 10.77 | 27.57 | >50 | 43.78 |

TABLE 6

Metabolic Stability of Test Compounds in Liver Microsomes of Different Species (a)

| Compound ID | Species | $T_{1/2}$ (min) | $CL_{int}$ (μL/min/mg protein) | Scaled-up $CL_{int}$ (mL/min/Kg) |
|---|---|---|---|---|
| Verapamil | Human | 13.32 | 104.07 | 130.53 |
| | Rat | 5.54 | 250.12 | 448.21 |
| | Mouse | 11.56 | 119.86 | 524.39 |
| Compound 1 | Human | 34.81 | 39.82 | 49.94 |
| | Rat | 16.00 | 86.61 | 155.20 |
| | Mouse | 35.36 | 39.20 | 171.50 |

TABLE 7

Metabolic Stability of Test Compounds in Liver Microsomes of Different Species (b)

| Compound ID | Species | Assay Format | 0 min | 15 min | 30 min | 45 min | 60 min |
|---|---|---|---|---|---|---|---|
| Verapamil | Human | With NADPH | 100.00 | 26.29 | 10.84 | 5.95 | 4.30 |
| | | Without NADPH | 100.00 | 88.70 | 84.00 | 83.50 | 90.40 |
| | Rat | With NADPH | 100.00 | 12.23 | 2.35 | 0.71 | 0.40 |
| | | Without NADPH | 100.00 | 102.19 | 92.87 | 91.71 | 97.12 |
| | Mouse | With NADPH | 100.00 | 15.30 | 6.34 | 3.32 | 2.42 |
| | | Without NADPH | 100.00 | 106.23 | 89.98 | 93.40 | 111.61 |
| Compound 1 | Human | With NADPH | 100.00 | 70.61 | 51.77 | 38.83 | 30.40 |
| | | Without NADPH | 100.00 | 98.20 | 92.81 | 89.22 | 103.59 |
| | Rat | With NADPH | 100.00 | 45.00 | 21.08 | 11.69 | 7.65 |
| | | Without NADPH | 100.00 | 95.03 | 90.68 | 91.30 | 102.48 |
| | Mouse | With NADPH | 100.00 | 72.40 | 51.67 | 37.39 | 32.04 |
| | | Without NADPH | 100.00 | 93.90 | 93.90 | 91.46 | 94.51 |

TABLE 8

Log D Results of Test Compound in 1-Octanol/PBS pH 7.4

| Compound ID | LogD Value |
|---|---|
| Progesterone | 3.78 |
| Compound 1 | 3.61 |

TABLE 9

Mitochondrial toxicity of the test compound in HepG2 cells

| Compound ID | $IC_{50}$ (μM)_Glucose | $IC_{50}$ (μM)_Galactose | Fold change in $IC_{50}$ |
|---|---|---|---|
| Compound 1 | >150 | >150 | — |
| Nefazodone | 77.22 | 6.82 | 11.33 |
| Digitonin | 4.30 | 1.79 | 2.40 |

* Compound precipitation observed for Compound 1 at 50 and 150 μM.

TABLE 10

Protein Binding Results of Test Compound in Human, Rat and Mouse Plasma

| | Human Plasma | | Rat Plasma | | Mouse Plasma | |
|---|---|---|---|---|---|---|
| Compound ID | % Bound | % Recovery | % Bound | % Recovery | % Bound | % Recovery |
| Ketoconazole | 98.33 | 101.01 | 99.63 | 100.83 | 99.33 | 104.25 |
| Compound 1 | 96.97 | 98.77 | 99.17 | 93.40 | 99.00 | 109.72 |

TABLE 11

Stability results of Compound 1 and control compounds in human, rat and mouse plasma

| Compound | Species | 0 min | 15 min | 30 min | 45 min | 60 min | 120 min |
|---|---|---|---|---|---|---|---|
| Propantheline | Human | 100.00 | 54.01 | 26.58 | 9.84 | 3.10 | 0.13 |
| Compound 1 | Human | 100.00 | 93.79 | 93.79 | 90.52 | 90.20 | 88.56 |
| Mevinolin | Rat | 100.00 | 3.78 | 0.00 | 0.00 | 0.00 | 0.00 |
| Compound 1 | Rat | 100.00 | 92.93 | 94.35 | 93.29 | 94.70 | 91.52 |
| Propantheline | Mouse | 100.00 | 74.15 | 64.03 | 48.07 | 37.61 | 14.60 |
| Compound 1 | Mouse | 100.00 | 96.17 | 96.17 | 97.56 | 96.17 | 93.73 |

TABLE 12

Solubility Results of Test Compound and Control Compound in PBS at pH 7.4

| Compound ID | Solubility (μM) |
|---|---|
| Progesterone | 13.88 |
| Compound 1 | 7.96 |

Csbl-1 Impairs ILK-PINCH-Parvin (IPP)-Mediated Actin Bundling In Vitro

Figure 4:
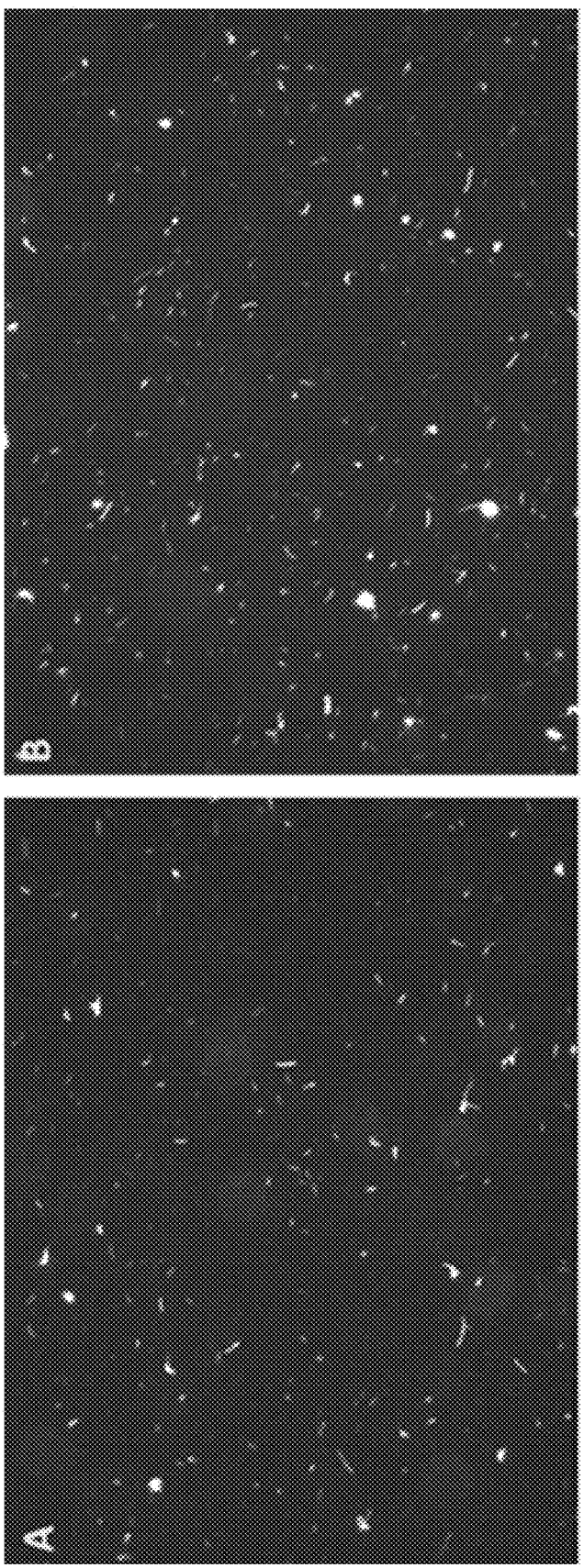
FIG. 4, panels A and B, show the effect of Csbl-1 (compound 1) on IPP-induced actin bundles. Panel A shows IPP-induced actin bundles (Mg2+; ATP=80 μM; 40 μM). Panel B shows increased numbers of smaller sizes as a result of Csbl-1 (Csbl-1: Mg2+; ATP=120 μM; 40 μM).

Next, we set out to obtain in vitro evidence of Csbl-1. It was recently showed that ILK-centered IPP complex promotes actin filament bundling (Vaynberg et al., 2017), which is mediated by two actin binding motifs in IPP as well as MgATP at the ILK pseudoactive site. Mutation of L207 into bulky Trp in ILK abolished the MgATP binding to ILK and impaired the formation and morphology of actin bundles (Vaynberg et al., 2018). Using the same actin bundling assay, we examined the effect of Csbl-1 on the IPP-mediated actin bundling. FIG. 4 shows that Csbl-1 caused the substantial change of IPP-induced actin bundles. In general, more bundles with smaller sizes were observed as a result of Csbl-1 interference. Csbl-1 would knock out MgATP at the ILK site and increase the local concentration of Mg', which may impact the actin bundling process (Tang and Janmey, 1996, Vaynberg et al., 2018). These data provide evidence for the effect of Csbl-1 in vitro, i.e., it alters ILK-mediated actin filament assembly.

Figure 5:
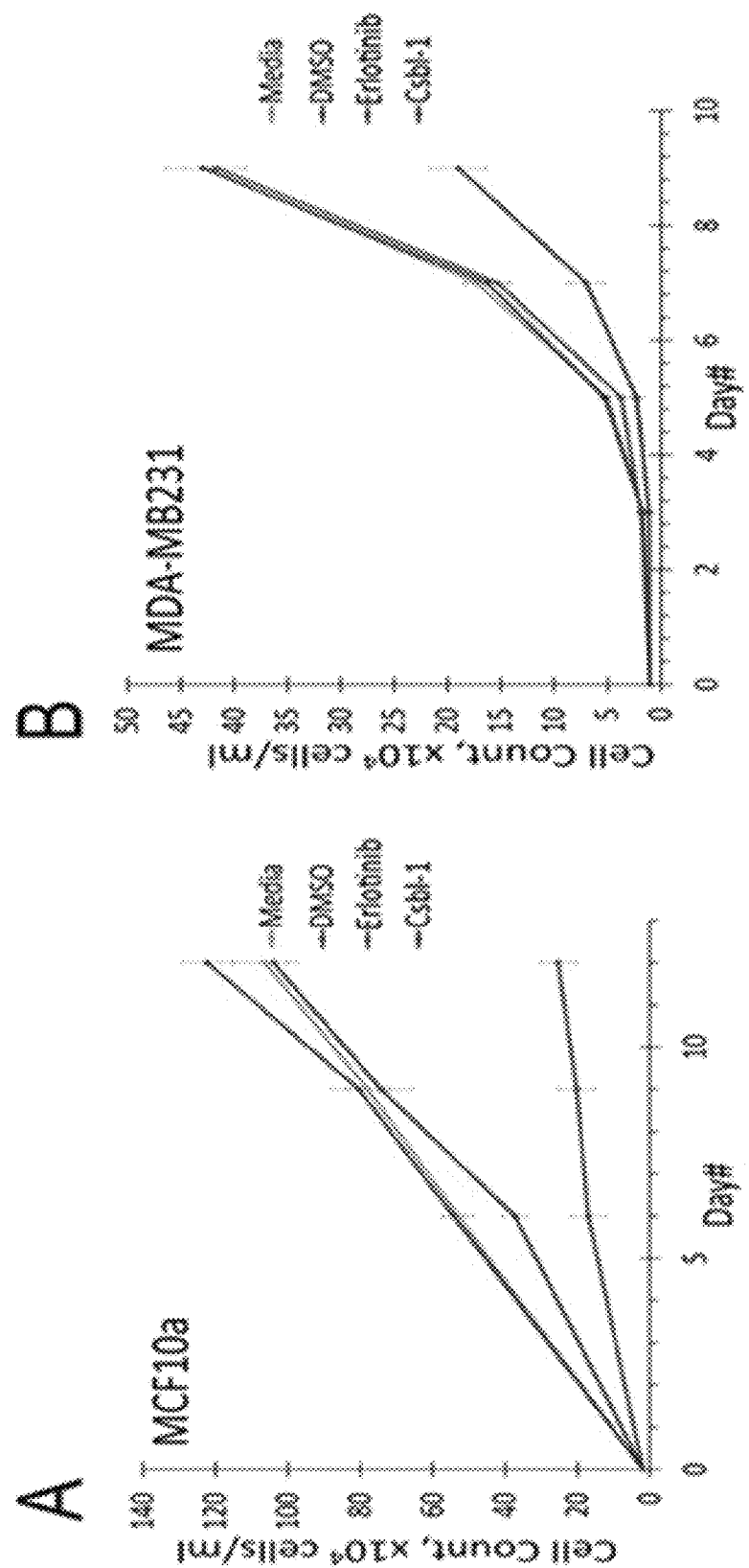
FIG. 5, panels A and B, show the effects of Csbl-1 and Erlotinib on cells. Panel A shows proliferation of normal breast MCF10a cells. Cells were seeded at 20,000 cells/ml in 12 well plates in complete media. On day 3, the compounds were added at final 2 μM and the cells were counted every 3 days. Panel B shows proliferation of triple negative breast cancer MDA-MB-231 cells. Cells were seeded at 10,000 cells/ml in 12 well plates in complete media. The compounds were added at final 2 μM on day 2 and the cells were counted every 2 days.

Csbl-1 Inhibits ILK-Mediated Proliferation of Triple Negative Breast Cancer (TNBC) Cell but not Normal Breast Cell Since ILK-dependent actin assembly regulates actin stress fibers, which in turn affects many cellular processes such as cell spreading, proliferation, and survival, we expected that Csbl-1 would interfere with ILK-dependent dysfunctional cellular behaviors. We therefore decided to examine the effect of Csbl-1 on MDA-MB-231—a triple negative breast cancer (TNBC) cell line. This cell line was chosen for the following reasons: (i) ILK is highly elevated in this metastatic cell line (see, FIG. 5a in Mongroo et al., 2004; FIG. 1E in Hsu et al., 2015; FIG. 1A in Qu et al., 2017)); (ii) it is a major type of TNBC cell line and has been extensively characterized (Holiday et al., 2011); (iii) currently there is no proven targeted therapy for TNBC (Denkert et al., 2017) so any effect of Csbl-1 would facilitate the development of therapeutics to treat this devastating disease. FIG. 5 panel A shows that Csbl-1 had little effect on MCF10a—non-tumorigenic epithelial breast cells whereas erlotinib exhibited significant toxicity to these cells probably due to off-target effects (Patricelli et al., 2011). By contrast, Csbl-1 substantially inhibited the proliferation of MDA-MB-231 whereas erlotinib had little effect at the same dose (FIG. 5 panel B). A dose-dependent titration indicated that the $IC_{50}$ of Csbl-1 on MDA-MB-231 is ~190 nM. These data provide strong evidence that Csbl-1 is specific to inhibit TNBC cells.

Csbl-1 Inhibits TNBC Tumor Growth Based on a Xenograft Model

Figure 6:
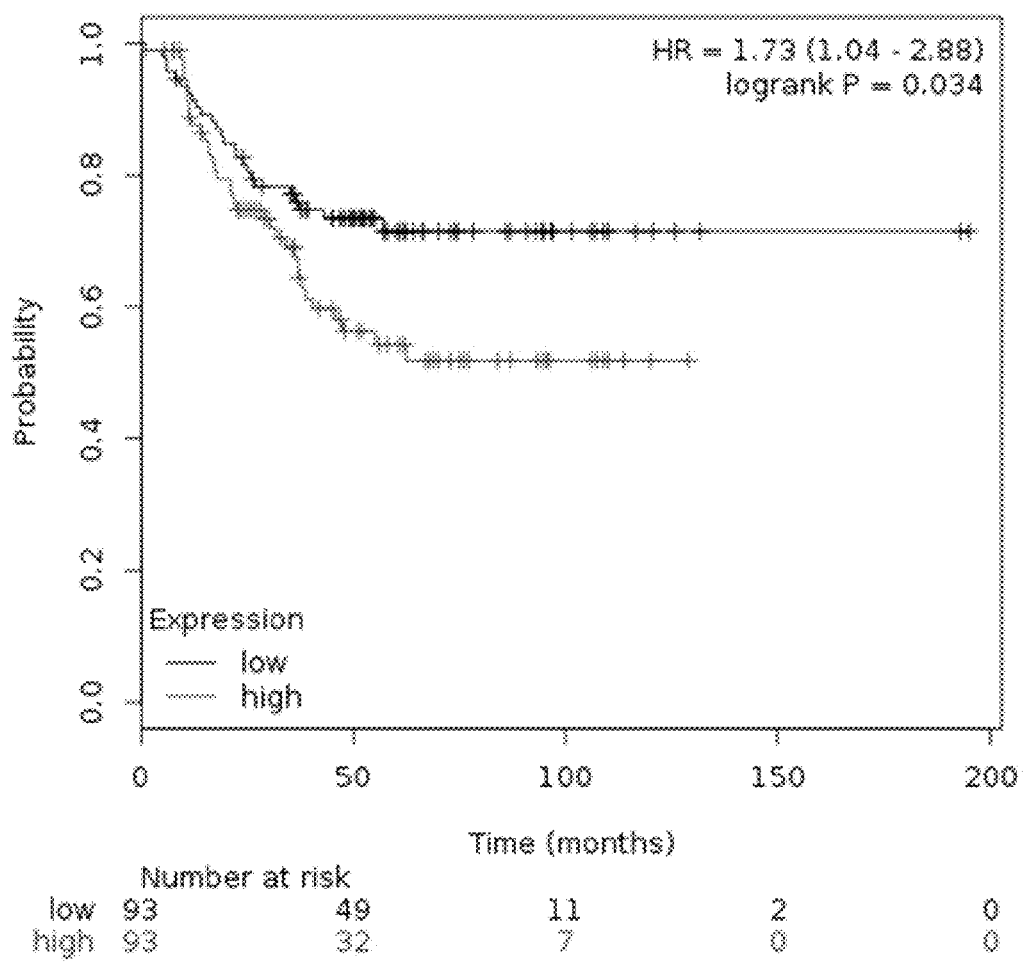
FIG. 6 shows the Kaplan-Meier (KM, http://followed by kmplot.com/analysis/) plot, which reveals the correlation of survival of 186 TNBC patients with ILK (Gene ID 201234_at) expression levels. The higher the ILK expression, the lower the patient survival.
Figure 7:
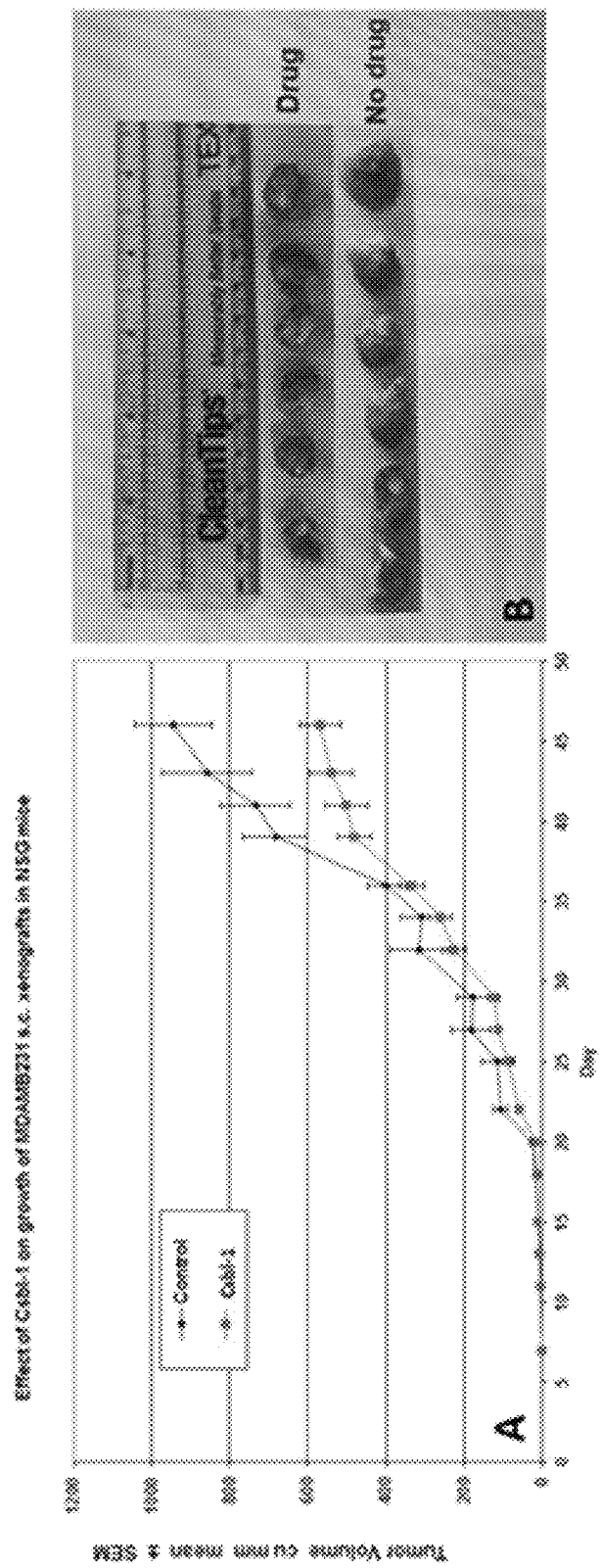
FIG. 7, panels A and B, show the effects of Csbl-1 (Compound 1) on TNBC in a xenograft model. Panel A shows results where 4 mice with TNBC tumors were treated by Csbl-1 at 100 mg/kg orally, five times per week starting at day 10. As compared to 4 control mice, TNBC tumors were substantially reduced after being treated by Csbl-1 with approximately 40% reduction in size at day 45. Panel B shows a tumor comparison at day 50 with and without Csbl-1 treatment.
Figure 8:
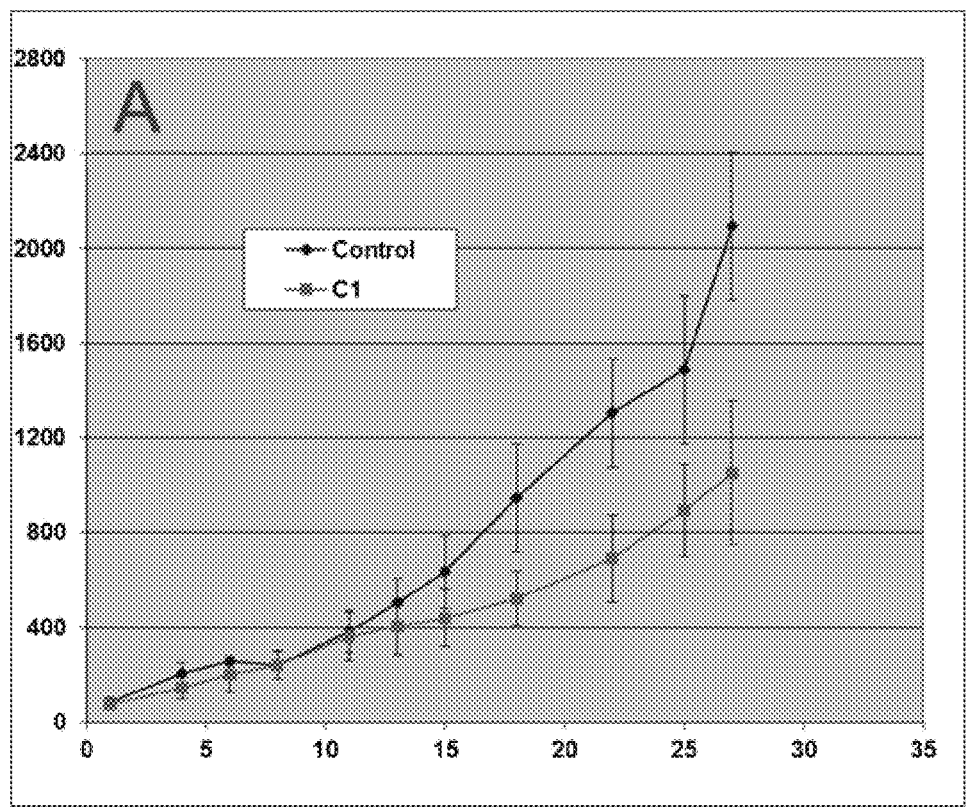
FIG. 8, panels A-C, show the effect of Csbl-1 on TNBC PDX mice. Csbl-1 was dissolved in olive oil. Five mice with TNBC were treated orally with Csbl-1 at 200 mg/kg five times/week vs 4 control mice without the treatment. Panel A shows tumors with the treatment by Csbl-1 (C1) were significantly reduced at day 27 vs the control mice. Panel B shows the representative tumors in control mice vs panel C where tumors were substantially reduced after the Csbl-1 treatment.
Figure 8:
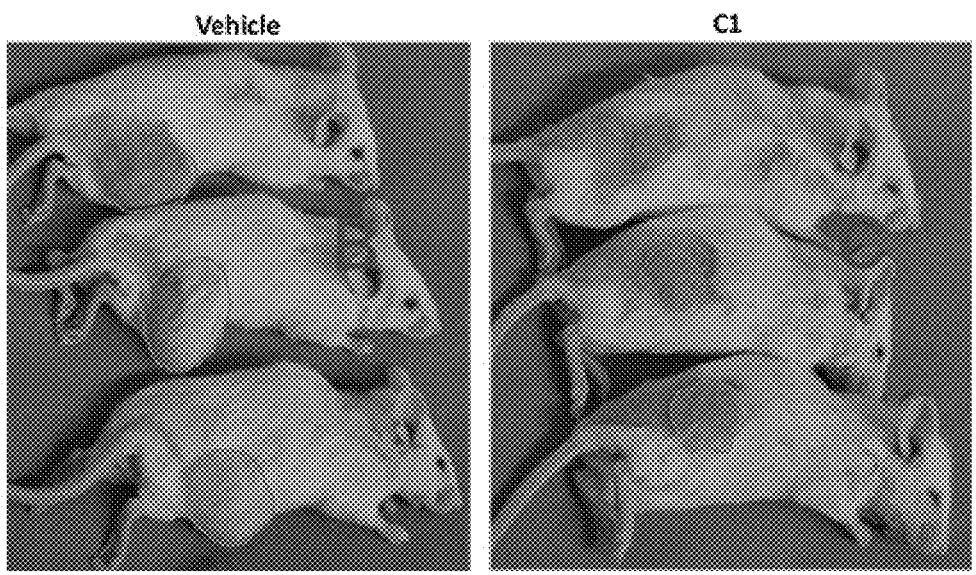

The next step was to evaluate the effect of Csbl-1 in mice bearing TNBC tumors. Given the fact that higher ILK expression level is correlated with poor outcome and reduced survival for TNBC patients (FIG. 6) and the above TNBC cell-based data, we decided to test whether Csbl-1 would be effective in suppressing the TNBC tumors in mice. Using Csbl-1 dissolved in CMC/TWEEN 80, normal mice were orally fed with 25 mg/kg, 50 mg/kg, 75 mg/kg, 100 mg/kg, 200 mg/kg, 400 mg/kg, and 510 mg/kg doses every day for two weeks and the mice were all fine with no toxic symptoms. Xenograft TNBC tumors were generated using MDA-MB231 on 8 mice. At $10^{th}$ day when the tumors were ~3 mm, 4 mice were fed with Csbl-1 at 100 mg/kg five times/week and the other 4 mice (control, no drug) had no Csbl-1 treatment. With no significant weight difference between the control mice fed with DMSO and mice fed with the compound Csbl-1. FIG. 7 shows that Csbl-1 significantly suppressed the TNBC tumor growth by ~40% at metastatic phase as compared to DMSO, which is consistent with the cell-based data in FIG. 5. We also examined the Csbl-1 effect on the mouse models with human derived patient TNBC tumor (PDX). FIG. 8 shows that Csbl-1 effectively inhibited TNBC tumor growth in PDX mice. These data provide in vivo evidence that Csbl-1 is a potent inhibitor of TNBC.

Example 3

Synthesis of Compounds

This Example describes exemplary synthesis protocols that could be employed to synthesize Csbl-1 (Compound 1) and Csbl-2 (Compound 8).

Scheme 1 synthesis of a compound (Csbl-1) of Formula I.

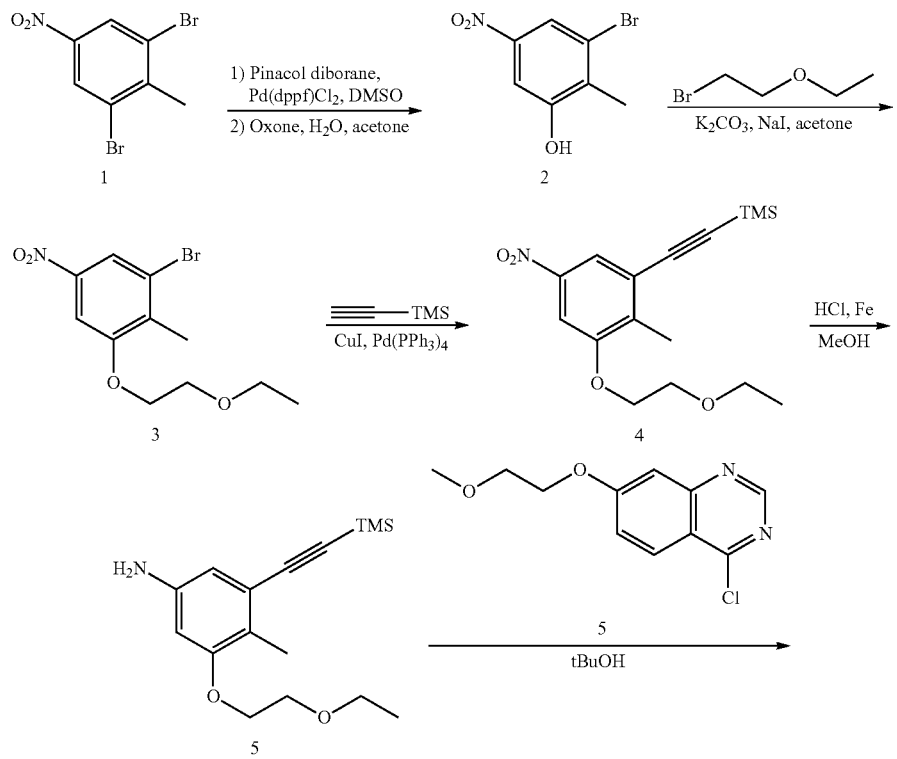

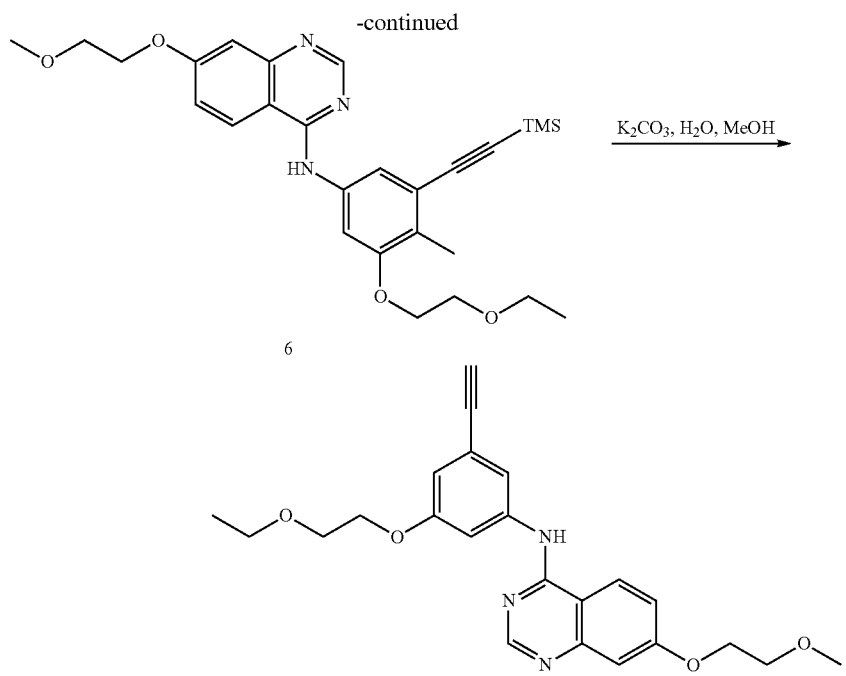
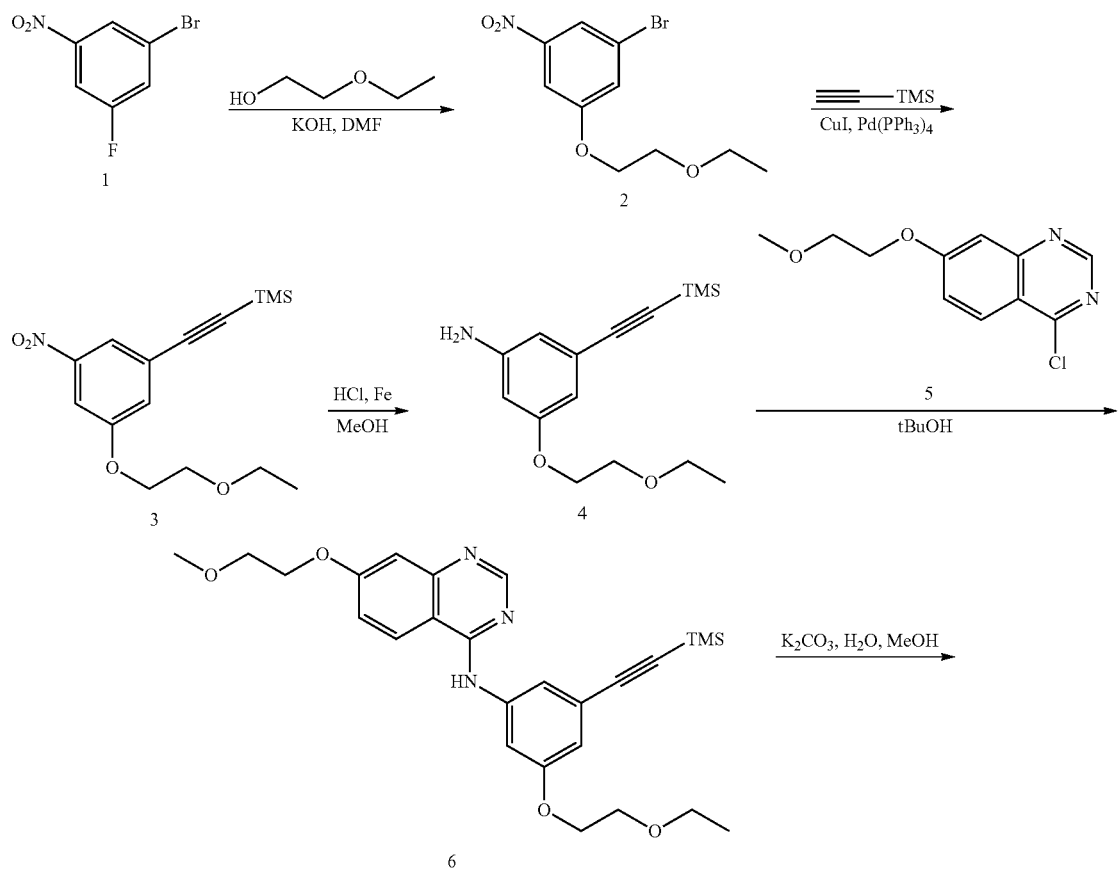
Scheme 2 large scale (e.g., 50-100 g) synthesis of a compound (Csbl-1)

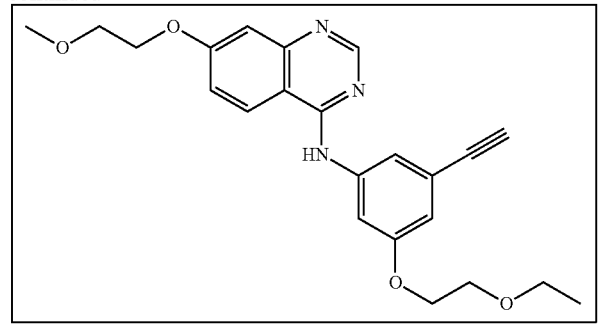
Csbl-01
50 g or 100 g, 95%
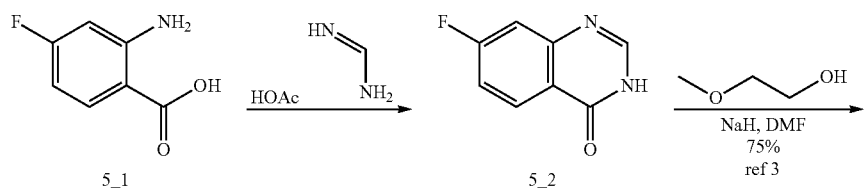
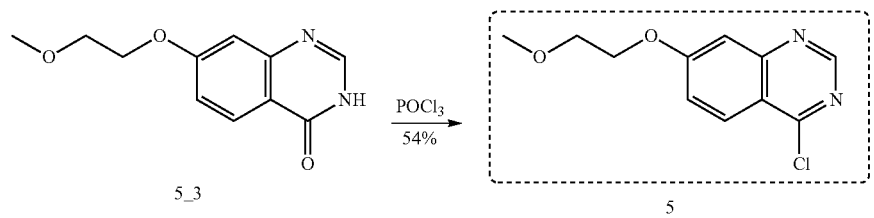
Scheme 3 synthesis of a compound (Csbl-2; aka Compound 8) of Formula II
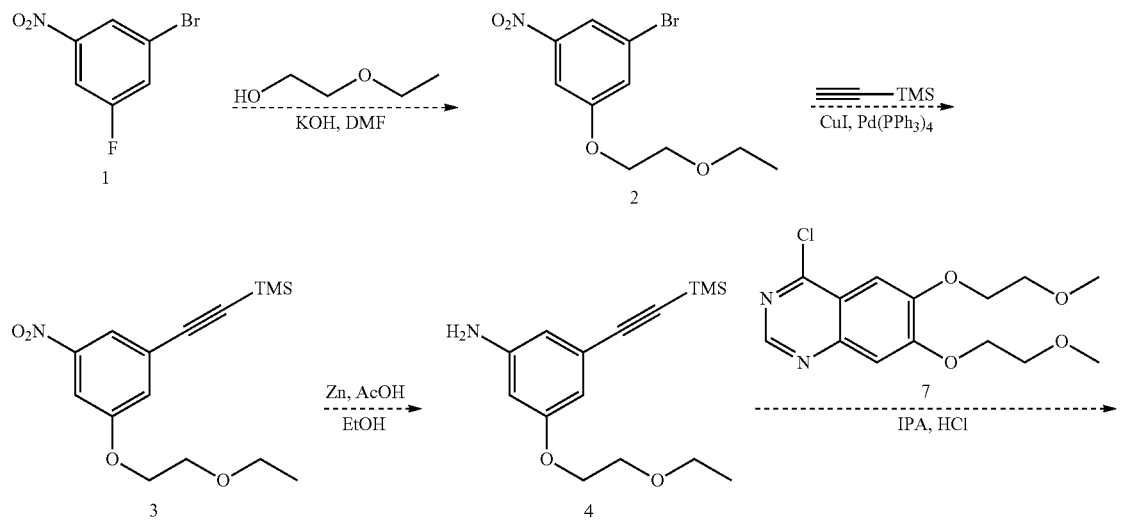

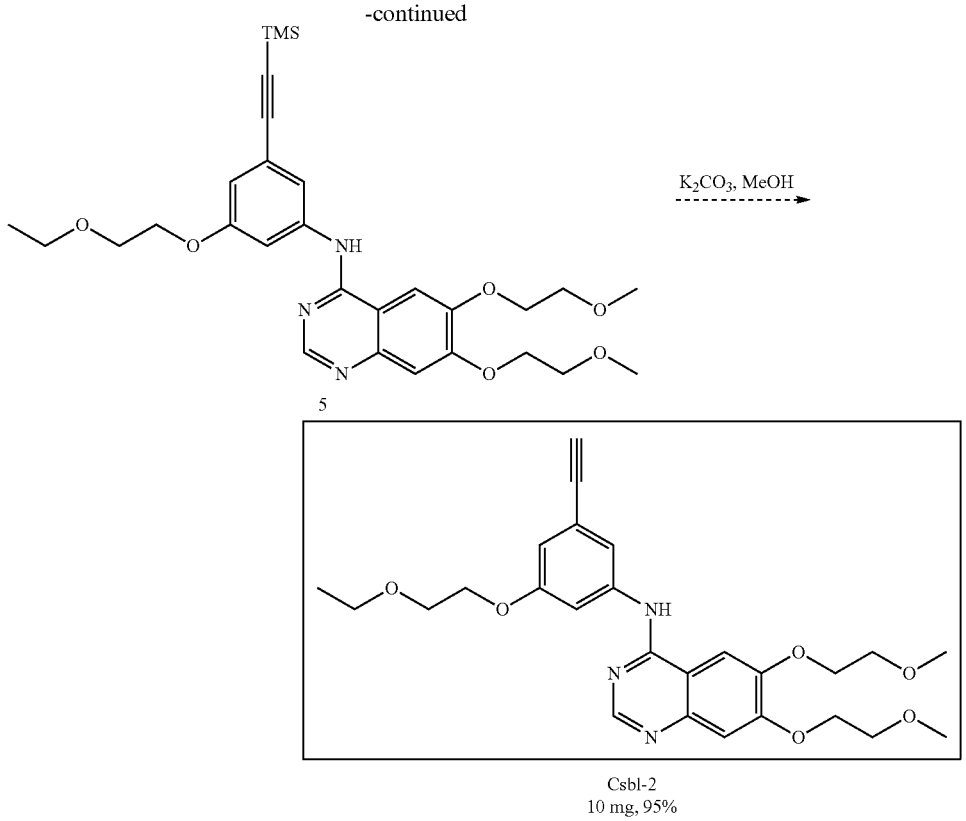

Csbl-2
10 mg, 95%

The synthesis of compounds of Formula I-VII can be achieved by skilled synthetic chemists using, for example, the procedures and intermediates exemplified above (see also Schnur and Arnold, 1998; Pandey et al., 2002; Li et al., 2013; Tung, 2015; all of which are herein incorporated by reference). Additional methods for synthesizing compounds of Formula I-VII including those within routes not explicitly shown in the above schemes are within the means of chemists of ordinary skill in the art.

REFERENCES

1. Augustin et al. (2013) Quantitative chemical proteomics profiling differentiates erlotinib from gefitinib in EGFR wild-type non-small cell lung carcinoma cell lines. Mol Cancer Ther. 12(4):520-9.
2. Cabodi et al., (2010) Integrin signalling adaptors: not only figurants in the cancer story. Nat Rev Cancer, 10(12):858-70,
3. Conradt et al., (2011) Disclosure of erlotinib as a multi-kinase inhibitor in pancreatic ductal adenocarcinoma, Neoplasia. 13(11):1026-34.
4. Denkert et al., Molecular alterations in triple-negative breast cancer-the road to new treatment strategies. Lancet. 389(10087):2430-2442, 2017.
5. Durbin et al., (2009) Oncogenic ILK, tumor suppression and all that JNK. Cell Cycle. 8(24):4060-6.
6. Fukuda et al., (2009) The pseudoactive site of ILK is essential for its binding to alpha-Parvin and localization to focal adhesions. Mol Cell, 36(5):819-30.
7. Fukuda et al., (2011) Biochemical, proteomic, structural, and thermodynamic characterizations of integrin-linked kinase (ILK): cross-validation of the pseudokinase. J Biol Chem., 286(24):21886-95.
8. Fukuda et al., Crystal structures of ILK hound to lung cancer drugs erlotinib and gefitinib. To be submitted, 2018 (attached).
9. Hannigan et al., (1996) Regulation of cell adhesion and anchorage-dependent growth by a new beta 1-integrin-linked protein kinase. Nature 379(6560):91-6.
10. Hannigan et al., (2005) Integrin-linked kinase: a cancer therapeutic target unique among its ILK. Nat Rev Cancer. 5(1):51-63.
11. Holliday and Speirs Choosing the right cell line for breast cancer research. Breast Cancer Research, 13:215, 2011.
12. Hsu et al. (2015) Function of integrin-Linked Kinase in Modulating the Sternness of IL-6-Abundant Breast Cancer Cells by Regulating γ-Secretase-Mediated Notch1 Activation in Caveolae. Neoplasia. 17(6):497-508.
13. Jantus-Lewintre et al., Analysis of the prognostic value of soluble epidermal growth factor receptor plasma concentration in advanced non-small-cell lung cancer patients. Clin Lung Cancer. 12(5):320-7, 2011.
14. Kim et al., (2015) Chelidonine suppresses migration and invasion of MDA-MB-231 cells by inhibiting formation of the integrin-linked kinaselPINCH/α-panin complex. Mol Med Rep. 12(2):2161-8.
15. Kitagawa et al., (2013) Activity-based kinase profiling of approved tyrosine kinase inhibitors. Genes Cells. 18(2): 110-22.
16, Lee et al., (2011) Identification and characterization of a novel integrin-linked kinase inhibitor. J Med Chem. 54(18):6364-74.
17. Legate et al., (2006) ILK. PINCH and parvin: the tIPP of integrin signalling. Nat Rev Mol Cell Biol. 7(1):20-31.

18. Li et al., (2013) One-dimensional self-assembly of phenylacetylene macrocycles: Effect of peripheral substituents. J. of Colloid and Interface Science, 395:99-103.
19. Mongroo et al., (2004) Beta-parvin inhibits integrin-linked kinase signaling and is downregulated in breast cancer. Oncogene. 23(55):8959-70.
20. Moyer et al. (1997) Induction of apoptosis and cell cycle arrest by CP-358,774, an inhibitor of epidermal growth factor receptor tyrosine kinase, Cancer Res. 57(21):4838-48.
21. Pandey et al., (2002) Identification of orally active, potent, and selective 4-piperazinylquinazolines as antagonists of the platelet-derived growth factor receptor tyrosine kinase family, J Med Chem, 4.5(17):3772-93
22. Pollard et al., RD. (2000) Molecular mechanisms controlling actin filament dynamics in nonmuscle cells. Annu Rev Biophys Biomol Struct 29, 545-76,
23. Patricelli et al. In Situ. Kinase Profiling Reveals Functionally Relevant Properties of Native Kinases. Chem Biol. 18(6):699-710, 2011.
24. Qu et al., (2017) ILK promotes cell proliferation in breast cancer cells by activating the PI3K/Akt pathway. Mol Med Rep. 16(4):5036-5042.
25. Schmidmaier and Baumann (2008) ANTI-ADHESION evolves to a promising therapeutic concept in oncology. Curr Med Chem. 15(10):978-90.
26. Schnur and Arnold (1998) Alkynyl and azido-substituted 4-anilinoquinazolines U.S. Pat. No. 5,747,498
27. Tang and Janmey (1996) The polyelectrolyte nature of F-actin and the mechanism of actin bundle formation. J Biol Chem. 271(15):8556-63.
28. Troussard et al, (2006) Preferential dependence of breast cancer cells versus normal cells on integrin-linked kinase for protein kinase B/Akt activation and cell survival. Cancer Res. 66(1):393-403.
29. Tung, R. (2015) Derivatives of Gefitinib U.S. Pat. No. 9,133,137
30. Vaynberg et al., (2018) Non-catalytic signaling by pseudokinase ILK for regulating cell adhesion. Nature Communications 9 (1), 4465.
31. Yoganathan et al. (2000) Integrin-linked kinase (ILK): a "hot" therapeutic target. Biochem Pharmacol, 60(8):1115-9,
32. Zeiler, M., Moser, M. & Mann, M. (2014) Copy number analysis of the murine platelet proteome spanning the complete abundance range. Mol Cell Proteomics 13, 3435-45,
33. U.S. Pat. No. 5,747,498
34. U.S. Pat. No. 8,575,339
35. U.S. Pat. No. 9,133,137
36. U.S. Pat. No. 8,309,133
37. European Pat. EP2628011

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. A compound having a structure of Formula V, or a salt thereof:

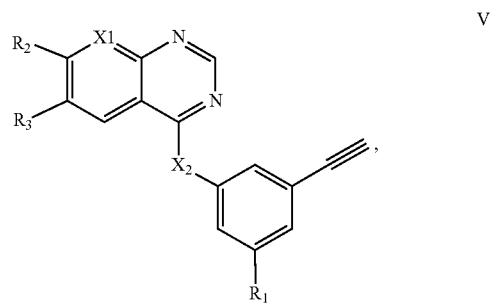

wherein:
$R_1$ is selected from: 2-methoxyethoxy, 2-ethoxyethoxy, 2-morpholinoethoxy, ethynyl, 2-(2-hydroxyethoxy)ethoxy, —O—CH$_2$CH$_2$CH$_2$OH, —O—CH$_2$CH$_2$—NO$_2$, —O—CH$_2$CH$_2$COOH, —O—CH$_2$CH$_2$—CONH$_2$, —O—CH$_2$CH$_2$—O—CH$_2$OH, —O—CH$_2$CH$_2$—O—CH$_2$CN, —O—CH$_2$CH$_2$—O—CH$_2$NH$_2$, —O—CH$_2$CH$_2$—O—CH$_2$NO$_2$, —O—CH$_2$CH$_2$—O—CH$_2$COOH, —O—CH$_2$CH$_2$—O—CH$_2$CF$_3$, and —O—CH$_2$CH$_2$—O—CH$_2$CONH$_2$;
$R_2$ is selected from: hydrogen, methoxy, and methoxyethoxy;
$R_3$ is selected from: hydrogen, methoxy, and methoxyethoxy;
X1 is N or CH; and
$X_2$ is selected from: NH, O, S, and CH$_2$.

2. The compound of claim 1, or a salt thereof, wherein $R_1$ is selected from: 2-methoxyethoxy, 2-ethoxyethoxy, 2-morpholinoethoxy, ethynyl, and 2-(2-hydroxyethoxy)ethoxy.

3. The compound of claim 1, or a salt thereof, wherein X1 is CH.

4. The compound of claim 1, or a salt thereof, wherein $X_2$ is NH.

5. A pharmaceutical composition comprising a compound of claim 1 or a pharmaceutically acceptable salt thereof, and a pharmaceutically acceptable carrier.

6. A method of treating triple negative breast cancer in a subject in need thereof, comprising administering a compound of claim 1 to the subject.

7. The method of claim 6, wherein the subject is a human.

8. The method of claim 6, wherein the compound is co-administered with an anti-cancer agent and/or an anti-inflammatory agent.

9. The method of claim 6, wherein the method comprises administering between 0.05-3000 mg of the compound to the subject.

10. The method of claim 6, wherein the method comprises administering between 25-600 mg of the compound to the subject.

11. The method of claim 6, wherein the method comprises administering 25-600 mg of the compound to the subject per day for at least two days.

* * * * *